US011351229B2

(12) United States Patent
Swann et al.

(10) Patent No.: US 11,351,229 B2
(45) Date of Patent: Jun. 7, 2022

(54) COMBINATION THERAPIES FOR TREATING INFANTILE SPASMS AND OTHER TREATMENT RESISTANT EPILEPSIES

(71) Applicant: Baylor College of Medicine, Houston, TX (US)

(72) Inventors: John W. Swann, Houston, TX (US); Chong L. Lee, Houston, TX (US); John T. Le, Houston, TX (US); James D. Frost, Jr., Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 16/606,087

(22) PCT Filed: Apr. 17, 2018

(86) PCT No.: PCT/US2018/027935
§ 371 (c)(1),
(2) Date: Oct. 17, 2019

(87) PCT Pub. No.: WO2018/195055
PCT Pub. Date: Oct. 25, 2018

(65) Prior Publication Data
US 2020/0171130 A1 Jun. 4, 2020

Related U.S. Application Data

(60) Provisional application No. 62/486,044, filed on Apr. 17, 2017.

(51) Int. Cl.
*A61K 38/30* (2006.01)
*A61P 25/08* (2006.01)
*A61K 31/197* (2006.01)

(52) U.S. Cl.
CPC ............ *A61K 38/30* (2013.01); *A61K 31/197* (2013.01); *A61P 25/08* (2018.01)

(58) Field of Classification Search
CPC ........ A61K 38/00; A61K 31/197; A61P 25/08
See application file for complete search history.

(56) References Cited

U.S. PATENT DOCUMENTS

| 2006/0251649 | A1* | 11/2006 | Gluckman | ........... | C07K 5/0202 424/143.1 |
|---|---|---|---|---|---|
| 2013/0058946 | A1 | 3/2013 | Zamoyski | | |
| 2016/0235718 | A1 | 8/2016 | Baraban | | |

FOREIGN PATENT DOCUMENTS

WO 2011126733 10/2011

OTHER PUBLICATIONS

Kwan and Brodie. "Combination Therapy in Epilepsy". Drugs 2006; 66 (14): 1817-1829. (Year: 2006).*
Bangalore et al. "Compliance and Fixed-dose Combination Therapy". Current Hypertension Reports 2007, 9:184-189 (Year: 2007).*
Schechter, PJ. "Clinical pharmacology of vigabatrin". Br. J. clin. Pharmac. (1989), 27, 19S-22S (Year: 1989).*
Glauser et al. "Evidence-Based Guideline: Treatment of Convulsive Status Epilepticus in Children and Adults: Report of the Guideline Committee of the American Epilepsy Society". Epilepsy Currents, vol. 16, No. 1 Jan./Feb. 2016 pp. 48-61 (Year: 2016).*
Dulac et al. "Vigabatrin in Childhood Epilepsy". Journal of Child Neurology, vol. 6, issue: 2_suppl, pp. 2S30-2S37, 1991 (Year: 1991).*
Robinson et al. "Guidance on dose level selection for regulatory general toxicology studies for pharmaceuticals". Laboratory Animal Science Association, 2009. (Year: 2009).*
Malmgren et al. "Vigabatrin Visual Toxicity: Evolution and Dose Dependence". Epilepsia, 42(5):609-615, 2001 (Year: 2001).*
Johnston et al. "Insulin-like Growth Factor-1 Is a Potent Neuronal Rescue Agent after Hypoxic-Ischemic Injury in Fetal Lambs". J Clin Invest. 1996;97(2):300-308 (Year: 1996).*
Gano et al. "MRI Findings in Infants With Infantile Spasms After Neonatal Hypoxic-Ischemic Encephalopathy". Pediatric Neurology 49 (2013) 401e405. (Year: 2013).*
UCB Pharma. "Epilepsy Seizures and Syndromes: Fact Sheet". (Year: 2008).*
Miltiadous et al. "IGF-1 ameliorates hippocampal neurodegeneration and protects against cognitive deficits in an animal model of temporal lobe epilepsy"; Experimental Neurology 231 (2011) 223-235 (Year: 2011).*
Klein et al. "Inter-individual variation in the effect of antiepileptic drugs in the intrahippocampal kainate model of mesial temporal lobe epilepsy in mice"; Neuropharmacology 90 (2015) 53-62. (Year: 2015).*
Guan et al. "Neuroprotective effects of the N-terminal tripeptide of insulin-like growth factor-1, glycine-proline-glutamate (GPE) following intravenous infusion in hypoxic-ischemic adult rats"; Neuropharmacology 47 (2004) 892-903 (Year: 2004).*
Wang et al. "Rational design and synthesis of an orally bioavailable peptide guided by NMR amide temperature coefficients", PNAS Dec. 9, 2014 111 (49) 17504-17509. (Year: 2014).*
Pisani et al. "Development of epilepsy in newborns with moderate hypoxic-ischemic encephalopathy and neonatal seizures"; Brain & Development 31 (2009) 64-68. (Year: 2009).*
Song et al., Neuroprotective levels of IGF-1 exacerbate epileptogenesis after brain injury. Sci. Rep. 6, 32095, 2016.*
Jiang et al., Insulin growth factor-1 (IGF-1) enhances hippocampal excitatory and seizure activity through IGF-1 receptor-mediated mechanisms in the epileptic brain. Clin. Sci (Lond) 129(12):1047-1060, 2015 (Abstract).*

(Continued)

*Primary Examiner* — Ruixiang Li
(74) *Attorney, Agent, or Firm* — Saul Ewing Arnstein & Lehr LLP; Kathryn Doyle; Domingos J. Silva

(57) ABSTRACT

The present invention provides methods of treating infantile spasms in a subject in need thereof. In certain embodiments, the method comprises administering to the subject both vigabatrin (VGB) and insulin-like growth factor 1 (IGF-1), a biologically active fragment thereof, or any derivative thereof.

21 Claims, 34 Drawing Sheets
Specification includes a Sequence Listing.

(56) References Cited

OTHER PUBLICATIONS

Kwan et al., "Combination Therapy in Epilepsy, When and What to Use", Drugs 2006; 66 (14): 1817-1829.
Bangalore et al., "Compliance and Fixed-dose Combination Therapy", Current Hypertension Reports, 2007, 9:184-189.
P. J. Schechter, "Clinical pharmacology of vigabatrin", Br. J. chn. Pharmac. (1989), 27, 19S-22S.
Glauser et al., "Evidence-Based Guideline: Treatment of Convulsive Status Epilepticus in Children and Adults: Report of the Guideline Committee of the American Epilepsy Society", Epilepsy Currents, vol. 16, No. 1 Jan./Feb. 2016 pp. 48-61.
Dulac et al., "Vigabatrin in Childhood Epilepsy", Journal of Child Neurology, vol. 6, Supplement 2, 1991, 8 pages.
Robinson, "Guidance on dose level selection for regulatory general toxicology studyes for pharmaceuticals", Laboratory Animal Science Association, 36 pages.
Malmgren et al., "Vigabatrin Visual Toxicity: Evolution and Dose Dependence", Epilepsia, 42(5):609-615, 2001.
Johnston et al., "Insulin-like growth factor-1 is a potent neuronal rescue agent after hypoxic-ischemic injury in fetal lambs", J Clin Invest. 1996;97(2):300-308. https://doi.org/10.1172/JCI118416.
Gano et al., "MRI Findings in Infants With Infantile Spasms After Neonatal Hypoxic-Ischemic Encephalopathy", Pediatric Neurology 49 (2013) 401-405.
UCB Pharma, "Epilepsy Seizures & Syndromes: Fact Sheet", 2008, 2 pages.

\* cited by examiner

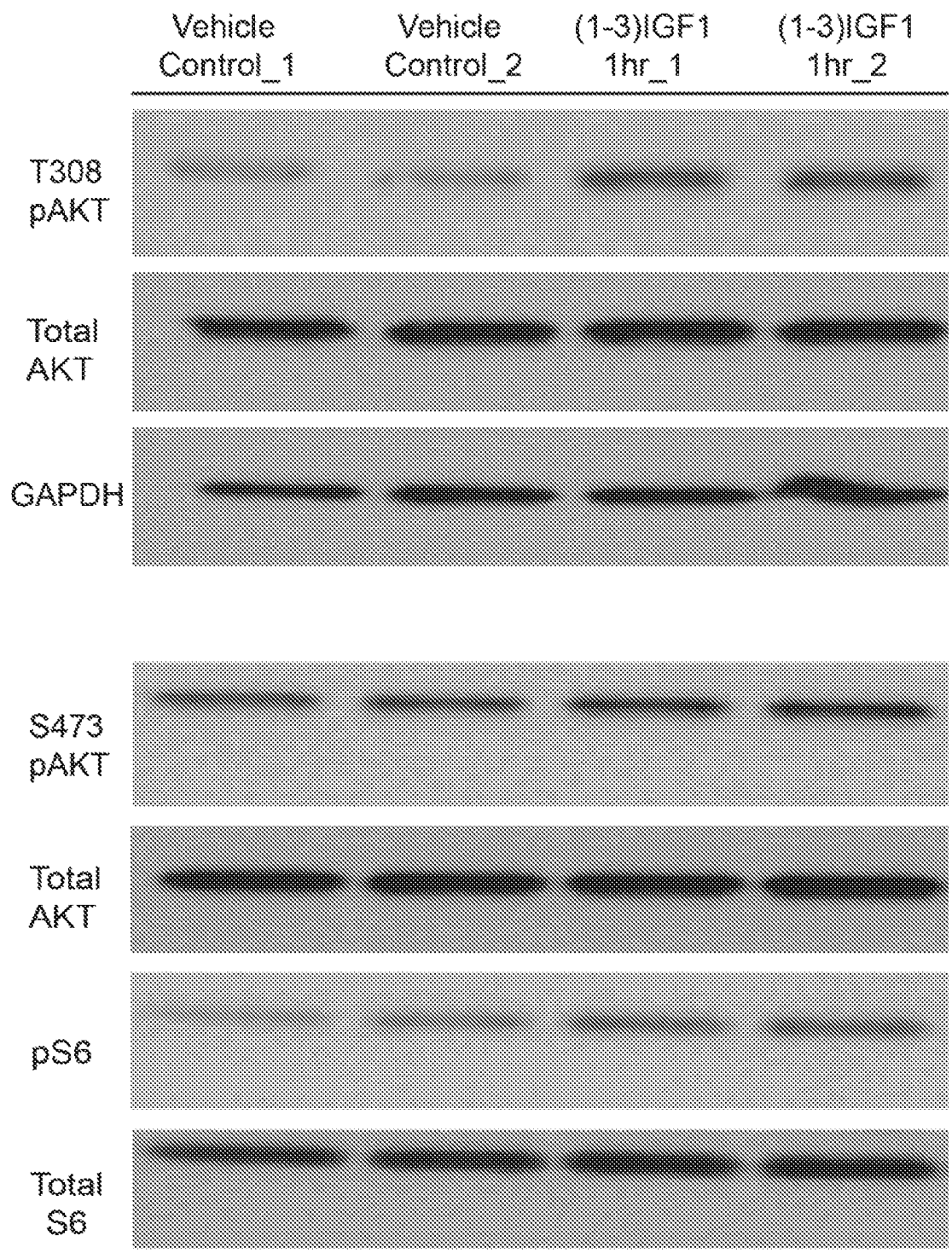

Control

Epileptic

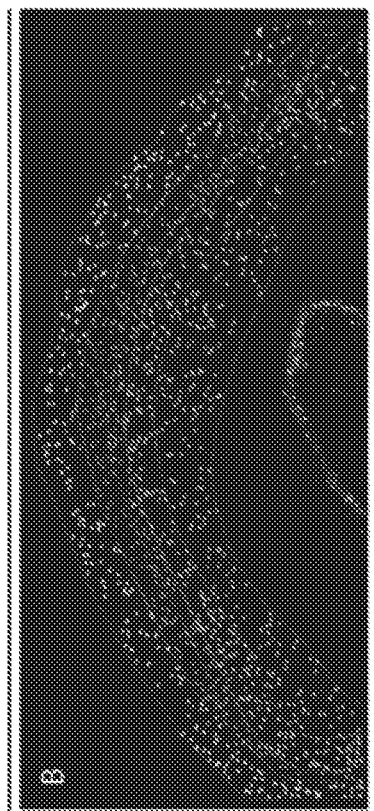
FIG. 11B
FIG. 11A
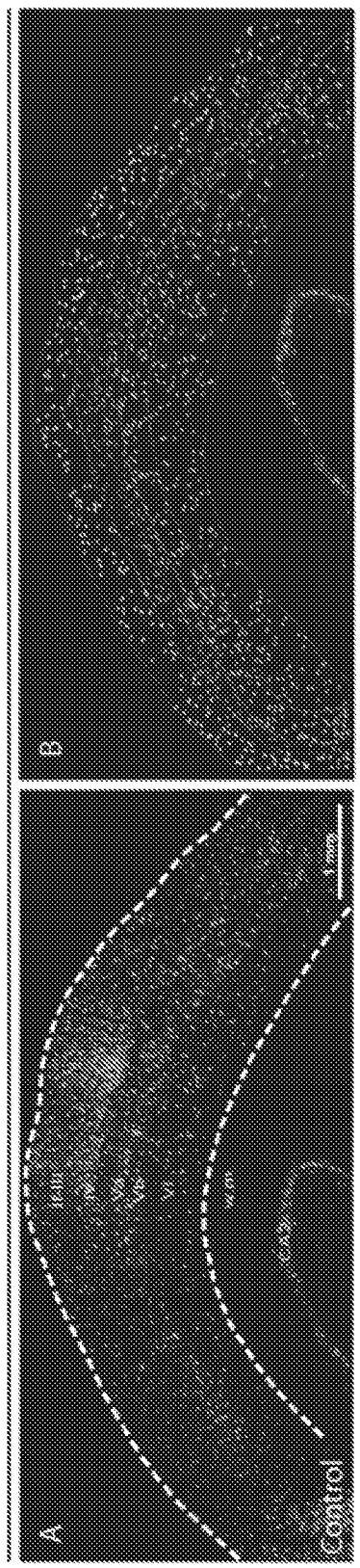
FIG. 11D
FIG. 11C
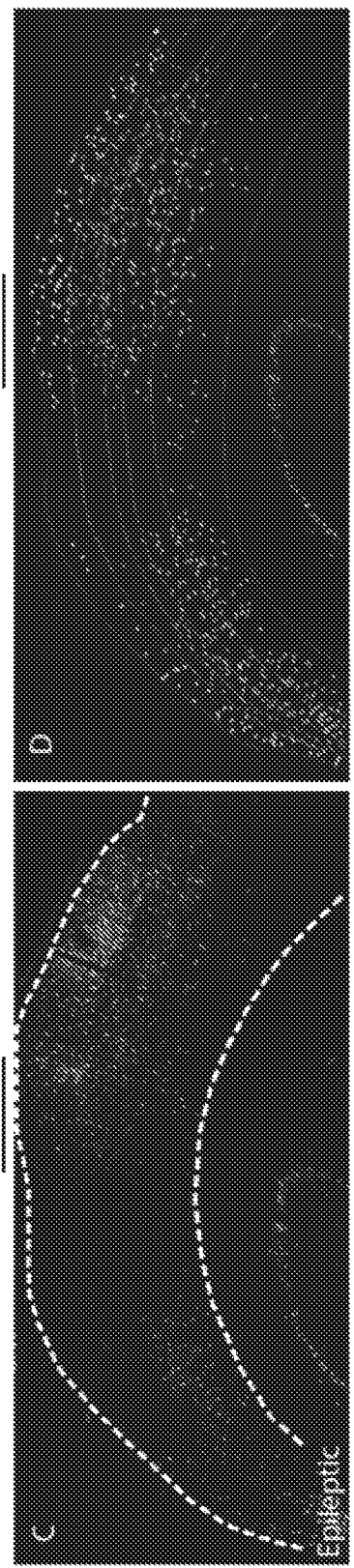

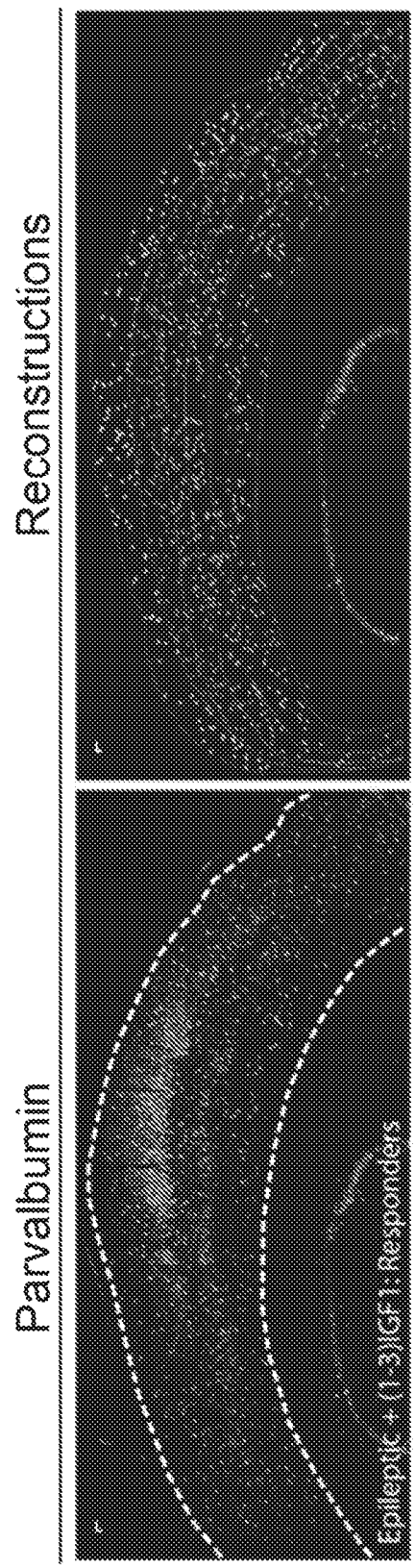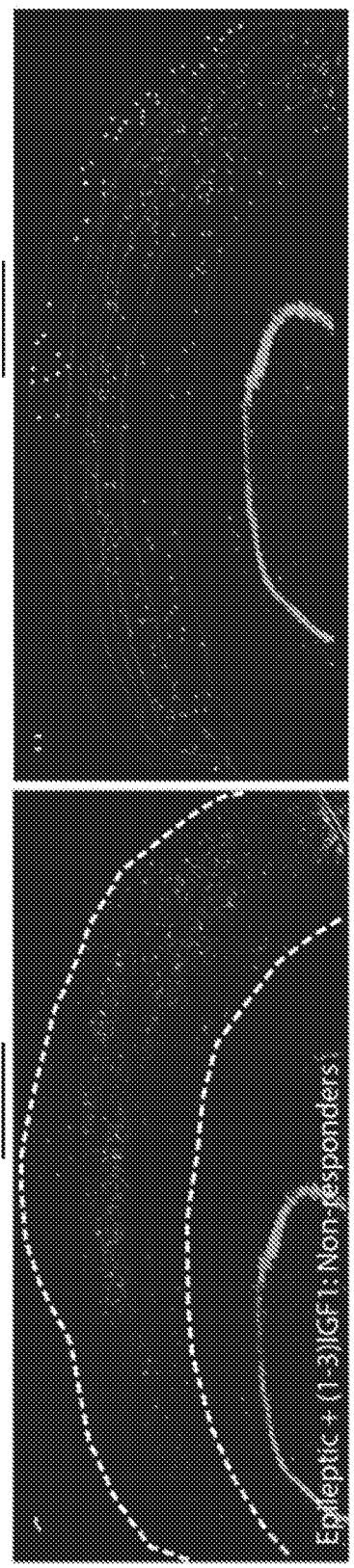

A control
B epileptic
C epileptic + (1-3)IGF1: responders
D epileptic + (1-3)IGF1: non-responders A control
B epileptic
C epileptic + (1-3)IGF1: responders
D epileptic + (1-3)IGF1: non-responders Induction of Infantile Spasms and Elimination by (1-3)IGF1
A Working Hypothesis At 2 Weeks Treatment

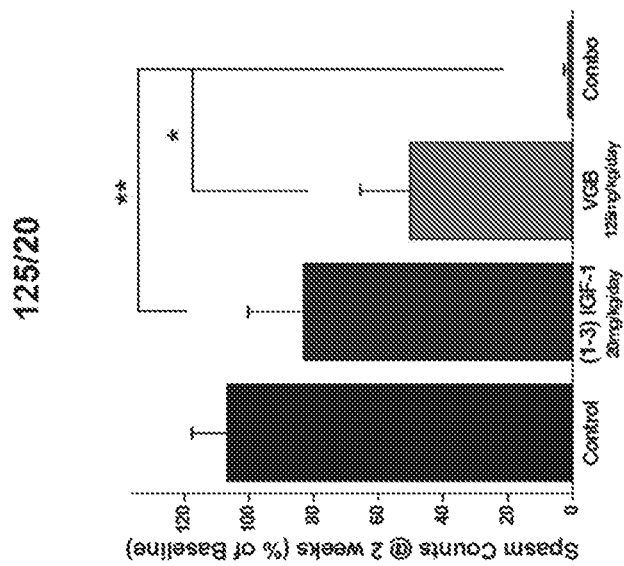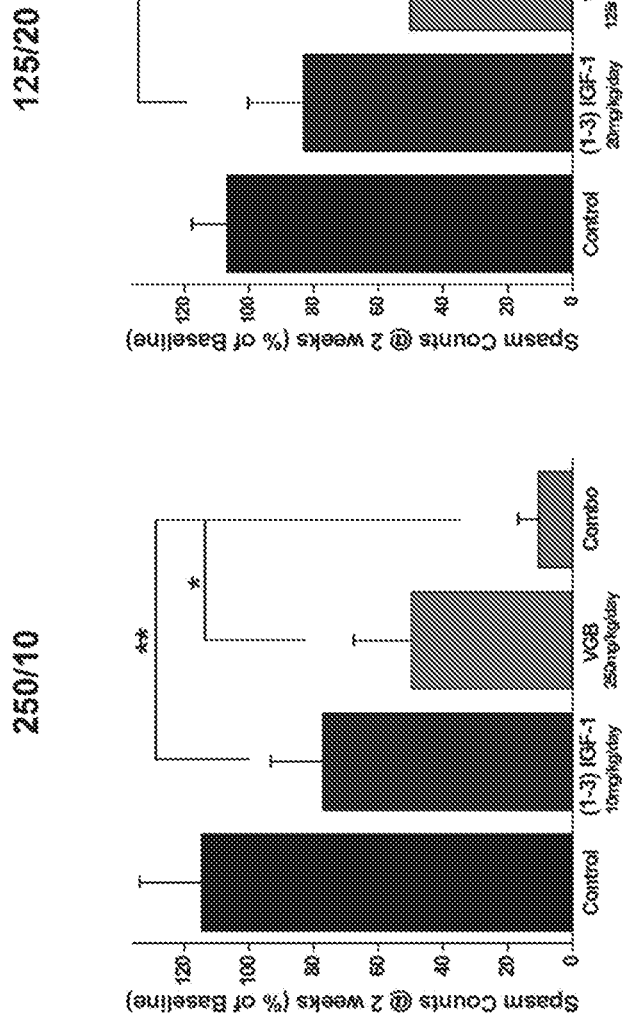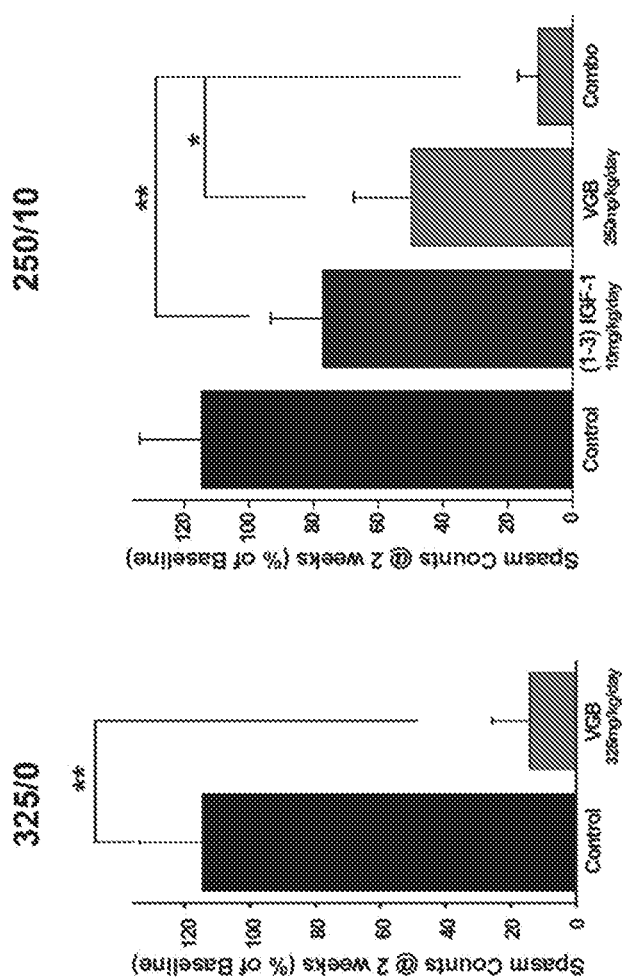

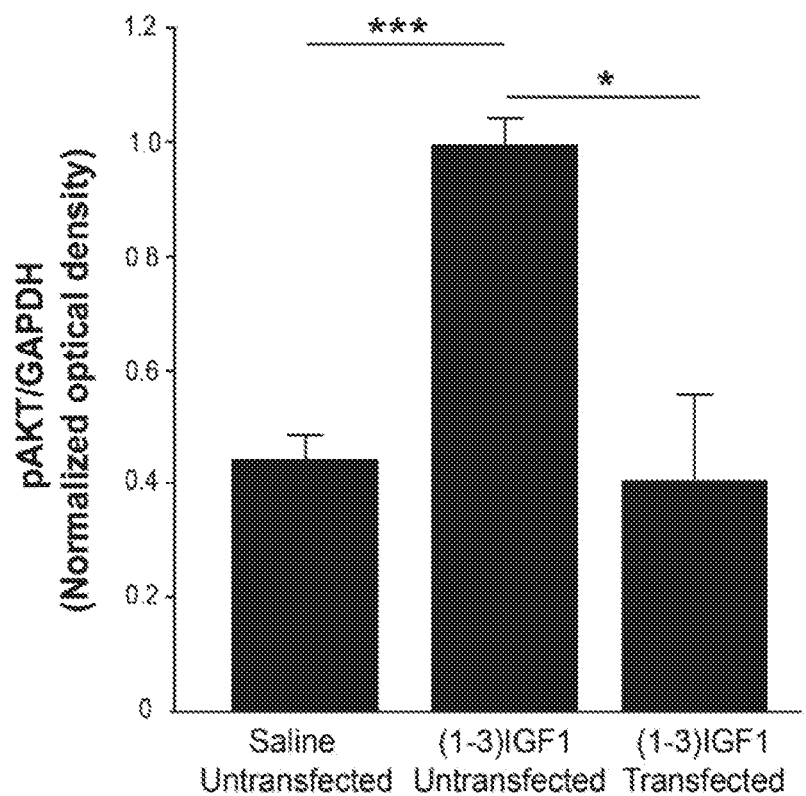
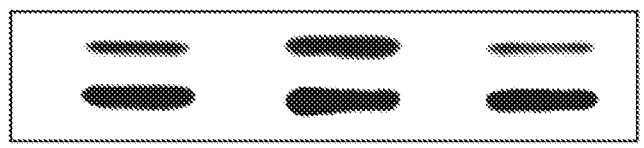

COMBINATION THERAPIES FOR TREATING INFANTILE SPASMS AND OTHER TREATMENT RESISTANT EPILEPSIES

CROSS-REFERENCE TO RELATED APPLICATIONS

This present application is a 35 U.S.C. § 371 national phase application from, and claims priority to, International Application No. PCT/US2018/027935, filed Apr. 17, 2018, which claims priority under 35 U.S.C. § 119(e) to U.S. Provisional Application No. 62/486,044, filed Apr. 17, 2017, all of which applications are incorporated herein by reference in their entireties.

BACKGROUND OF THE INVENTION

Infantile spasms are a severe seizure disorder that occurs in young children, with an average age of onset of about 6 months. Infantile spasms affect approximately 1 in every 2,300 live births, and long term prognosis is usually quite poor, leading to intractable epilepsy and learning impairment. There are over 200 disparate conditions associated with infantile spasm seizure disorders, including central nervous system infection, developmental brain abnormalities, cortical dysplasia, hypoxic-ischemic encephalopathy and single gene mutations, such as TSC1/2 and ARX. The symptoms of infantile spasms can be either violent or subtle. Infantile spasms can manifest as brief bilateral jerking contractions of muscles of the extremities, neck and/or trunk, and often occur in clusters. Further, intellectual disabilities commonly develop in children suffering from infantile spasms.

The current standard of care includes administration of adrenocorticotropic hormone (ACTH) and vigabatrin (γ-vinyl-GABA, 4-aminohex-5-enoic acid, or VGB). Usually one of these drugs is administered as the first treatment, and if that fails, the patient is switched to the other drug. Unfortunately, approximately 30% of children do not respond to either drug, and even for those who do, both drugs can have severe side effects, such as renal complications, peripheral retinopathy, teratogenicity, and neurotoxicity. The severity of side effects can increase when ACTH and VGB are co-administered. Further, while ACTH and VGB can prevent the spasms, they often do not prevent the intellectual disabilities and other forms of intractable epilepsy that develop as the children grow.

There thus remains a need in the art for novel effective methods of treating infantile spasms. In certain embodiments, these methods should treat infantile spasms without the risk of severe side effects. In other embodiments, these methods should also prevent the development of intellectual disabilities. The present invention meets these needs.

BRIEF SUMMARY OF THE INVENTION

The invention provides a method of treating or preventing treatment-resistant seizures in a subject in need thereof.

In certain embodiments, the method comprises administering to the subject a therapeutically effective amount of vigabatrin and a therapeutically effective amount of an IGF-1 agent.

In certain embodiments, the method comprises administering to the subject a therapeutically effective amount of an IGF-1 agent, wherein the subject is not administered any other agent that treats or prevents seizures.

In certain embodiments, the subject suffers from one or more treatment-resistant seizure causing disorders selected from the group consisting of infantile spasms, refractory complex partial epilepsy, secondary generalized seizures, temporal lobe epilepsy, simple partial seizures, and refractory seizures.

In certain embodiments, the IGF-1 agent is IGF-1, or a fragment, derivative, salt, or solvate thereof.

In certain embodiments, the IGF-1 agent is Gly-Pro-Glu [GPE], des(1-3)IGF-1, cyclic Pro-Gly [cPG] or a derivative, enantiomer, diastereoisomer, salt, or solvate thereof.

In certain embodiments, the vigabatrin and the IGF-1 agent are administered simultaneously to the subject. In other embodiments, the vigabatrin and the IGF-1 agent are co-formulated in a pharmaceutical composition.

In certain embodiments, the IGF-1 agent is administered orally to the subject. In other embodiments, the vigabatrin is administered orally to the subject.

In certain embodiments, the vigabatrin and the IGF-1 agent are co-formulated for oral administration to the subject.

In certain embodiments, the vigabatrin is administered to the subject before the IGF-1 agent. In other embodiments, the vigabatrin is administered to the subject after the IGF-1 agent.

In certain embodiments, the vigabatrin is administered to the subject in a dose of about 50 mg/kg/day to about 400 mg/kg/day. In other embodiments, the vigabatrin is administered to the subject in a dose of about 100 mg/kg/day to about 250 mg/kg/day. In yet other embodiments, the vigabatrin is administered to the subject in a dose of about 125 mg/kg/day. In yet other embodiments, the IGF-1 agent is administered to the subject in a dose of about 1 mg/kg/day to about 200 mg/kg/day. In yet other embodiments, the IGF-1 agent is administered to the subject in a dose of about 20 mg/kg/day.

In certain embodiments, the therapeutically effective amount of vigabatrin when administered in conjunction with the IGF-1 agent is lower than a therapeutically effective amount of vigabatrin to be administered in the absence of the IGF-1 agent. In other embodiments, the therapeutically effective amount of the IGF-1 agent when administered in conjunction with vigabatrin is lower than a therapeutically effective amount of the IGF-1 agent to be administered in the absence of vigabatrin. In yet other embodiments, the subject suffers a reduced or negligible vigabatrin-related side effect, as compared to treatment with vigabatrin in the absence of the IGF-1 agent. In yet other embodiments, the vigabatrin-related side effect is at least one selected from the group consisting of retinotoxicity, visual field loss, neurotoxicity, peripheral neuropathy, renal complications, drowsiness, headache, dizziness, anxiety, depression, memory loss, impairment of cognitive development, diplopia, aggression, ataxia, vertigo, hyperactivity, vision loss, retinal nerve fiber damage, confusion, insomnia, impaired concentration, speech disorders, irritability, tremors, emotional lability, and abnormal gait. In yet other embodiments, the vigabatrin-related side effect is at least one from the group consisting of retinotoxicity and visual field loss.

In certain embodiments, the subject experiences more than about 90% spasm reduction upon the administering. In other embodiments, the subject experiences more than about 95% spasm reduction upon the administering. In yet other embodiments, the subject experiences about 100% spasm reduction upon the administering.

In certain embodiments, the subject is a mammal. In other embodiments, the subject is a human.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIG. 1A comprises an image from a control animal that did not have epilepsy and illustrates the wide dispersion and high expression of IGF-1 in normal cortex. FIG. 1B comprises a very high magnification image of the soma of a single nerve cell from a control animal showing the distribution of IGF-1 (green) in what are likely protein transport vesicles. Vesicles stained red contain transferrin receptor, a marker for another subpopulation of protein transport vesicles. FIG. 1C comprises an image of the neocortex from an epileptic animal illustrating reduced expression of IGF-1.

FIG. 5 comprises a series of images of western blots showing activation of the IGF-1R-PI3K-AKT signaling cascade in the neocortex 1 hour after parenteral injection of the (1-3)IGF1 peptide in a subject. Total expression levels of AKT and S6 were unchanged and served as controls, as did the expression of the gel loading control GAPDH.

FIGS. 6A-6B comprise images comparing the expression of parvalbumin by immunohistochemistry. FIG. 6C comprises a graph quantifying the difference in parvalbumin levels in a group of control and epileptic subjects. FIGS. 6D-6E comprise images comparing the expression of calretinin, a biomarker for a different inhibitory interneuron population, in a control and epileptic subject. FIG. 6F comprises a graph quantifying the difference in calretinin levels from immunohistochemically stained sections.

FIG. 8A comprises a graph reporting daily spasm counts averaged at weekly intervals and normalized to baseline counts in each subject. In a group of 10 control subjects, spasm frequency increased slightly over the 5 weeks of recordings. Spasm frequency in 8 rats treated with (1-3)IGF-1 (10 mg/kg/day) gradually decreased over the same time period and reached approximately 30% of baseline levels. FIG. 8B comprises a graph reporting that 5 of 8 (1-3)IGF-1 treated rats became free of spasms. All control rats continued to have frequent spasms.

FIG. 9A comprises a recording before treatment (i.e. at baseline), where the hypsarrhythmic pattern was present but was eliminated after treatment with (1-3)IGF-1 (FIG. 9B).

FIG. 11A-11H comprise a set of images of parvalbumin expression in: (FIGS. 11A-11B) control rats, (FIGS. 11C-11D) rats with epileptic spasms, (FIGS. 11E-11F) epileptic rats treated with (1-3)IGF-1 that responded with cessation of spasms, and (FIGS. 11G-11H) epileptic rats treated with (1-3)IGF-1 that did not completely respond to treatment. FIGS. 11A, 11C, 11E, and 11G show parvalbumin immunohistochemical stains of the neocortex from one representative animal in the 4 groups. FIGS. 11B, 11D, 11F, and 11H comprise Neurolucida computer reconstructions of the number and location of each parvalbumin nerve cell in the corresponding immunohistochemical stain image. The images and drawings show that parvalbumin levels are reduced in epileptic subjects, but with treatment with (1-3) IGF-1 the expression of parvalbumin recovers in drug responders but not in animals that continued to have spasms.

Figure 13:
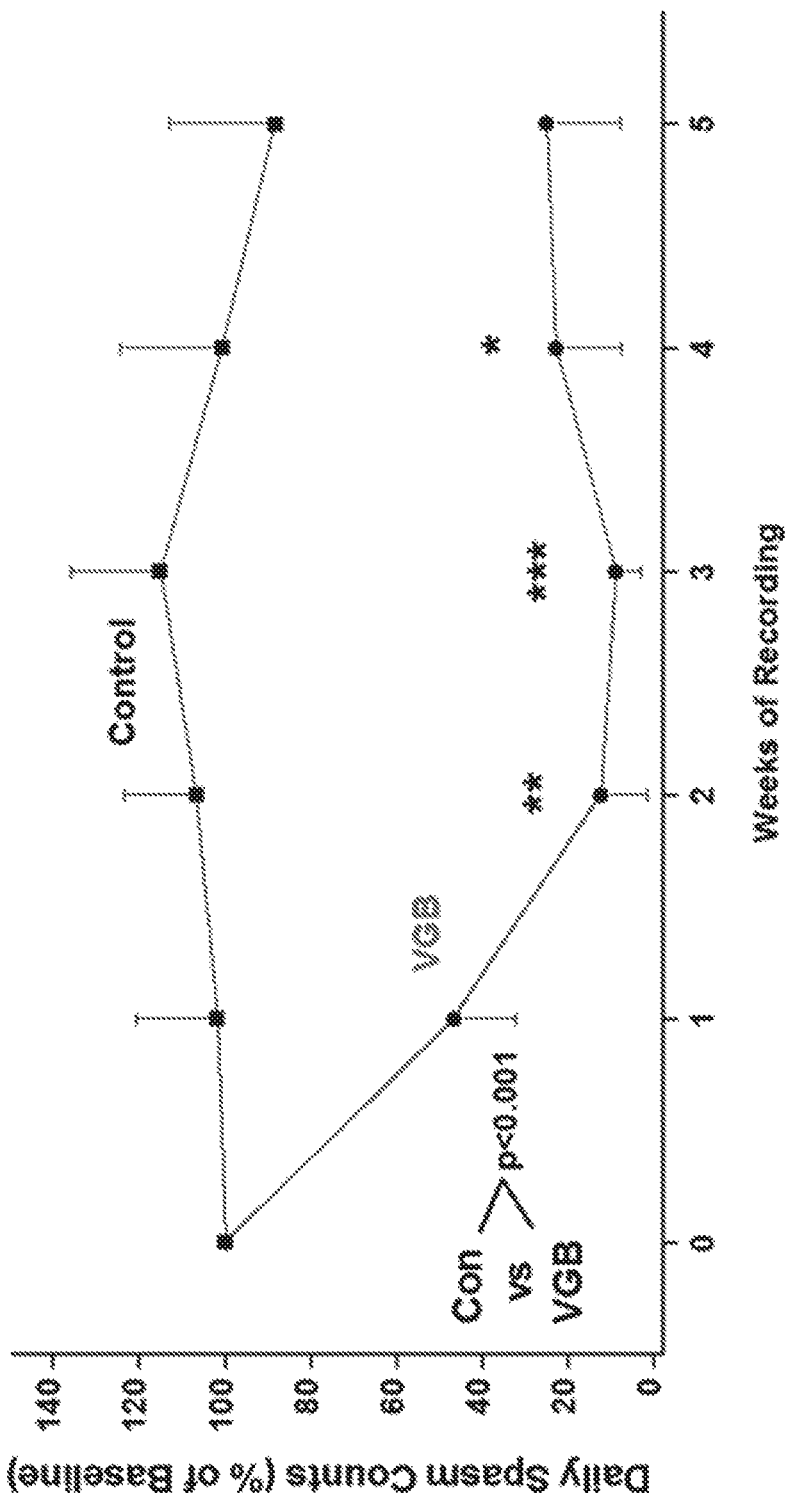

FIG. 13 comprises a graph showing suppression of spasms by administration of VGB. In a group of subjects, VGB was injected daily at a dose of 325 mg/kg/day (i.p.) for 2 weeks. Spasms were counted from continuous 24 hours/day, 7 days/week video/EEG recordings. Control rats received the drug vehicle. VGB was effective at this high dose in suppressing spasms, while control animals continued to have frequent spasms.

Figure 9A:
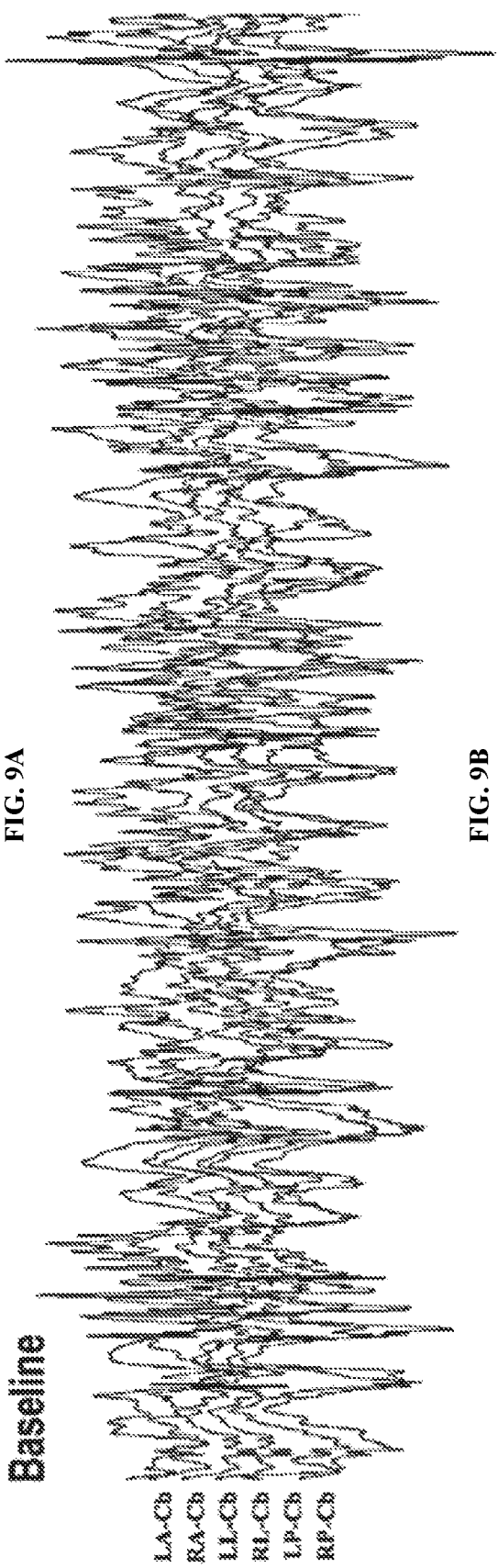
FIGS. 9A-9B comprise EEG recordings comparing hypsarrhythmia neural activity in a subject suffering from spasms before and after treatment with (1-3)IGF-1.
Figure 9B:
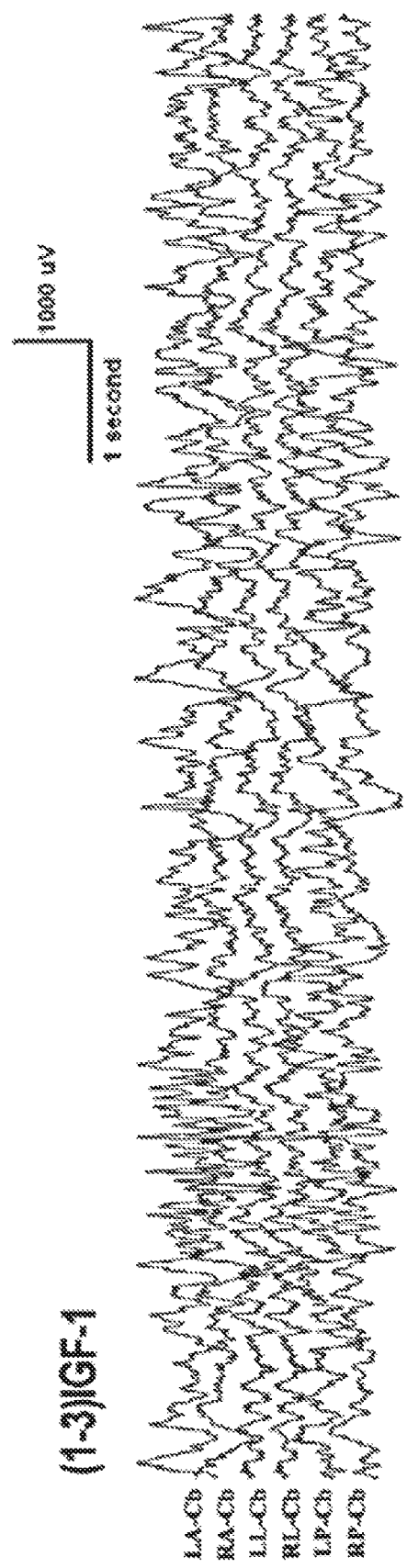
Figures 14A, 14B:
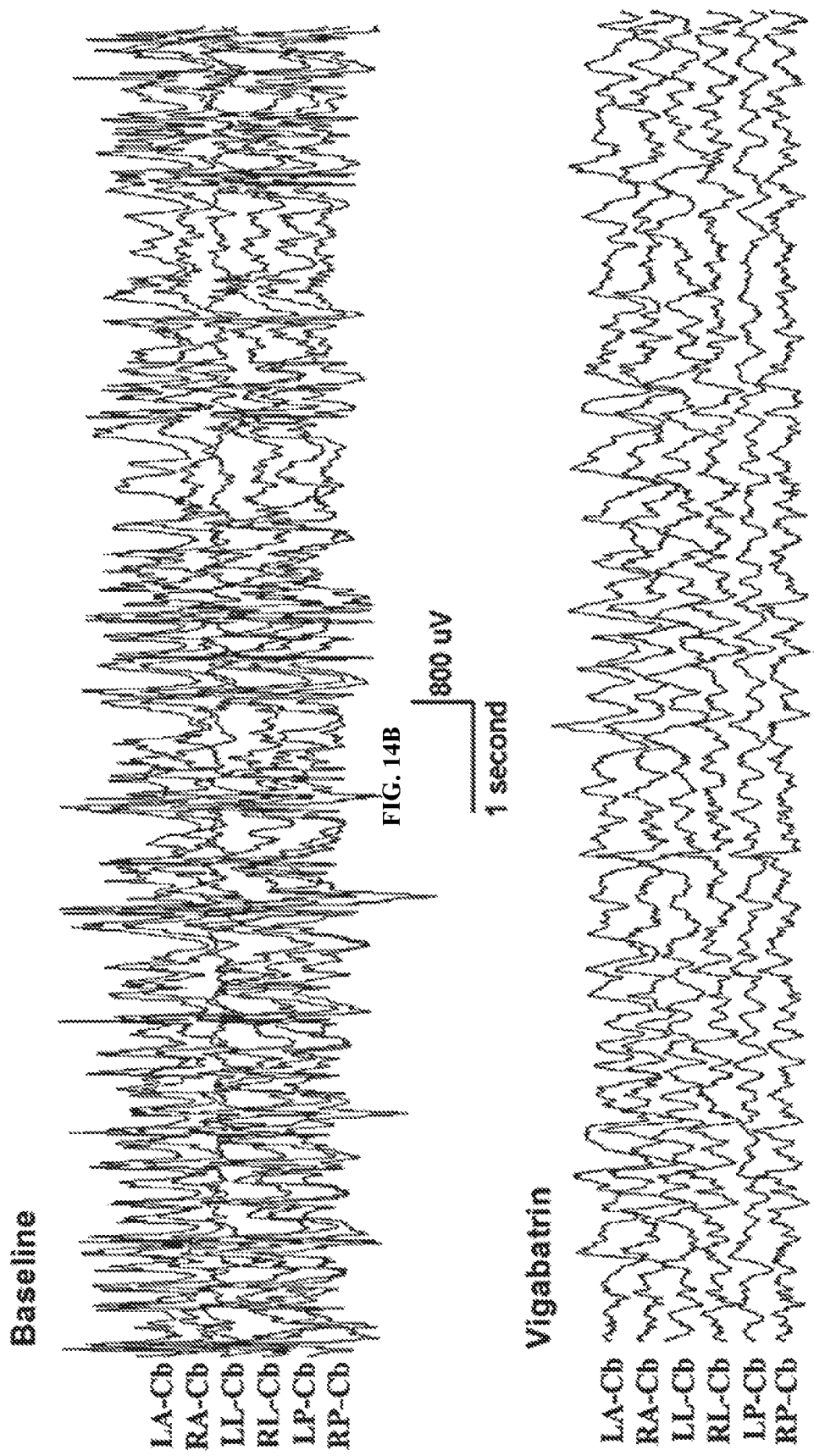

FIGS. 14A-14B comprise EEG recordings comparing hypsarrhythmia neural activity in a subject suffering from spasms before and after treatment with VGB. FIG. 14A is a recording before treatment (i.e. at baseline), where the hypsarrhythmic pattern was present but was eliminated after 2 weeks of VGB treatment (FIG. 9B).

Figure 14D:
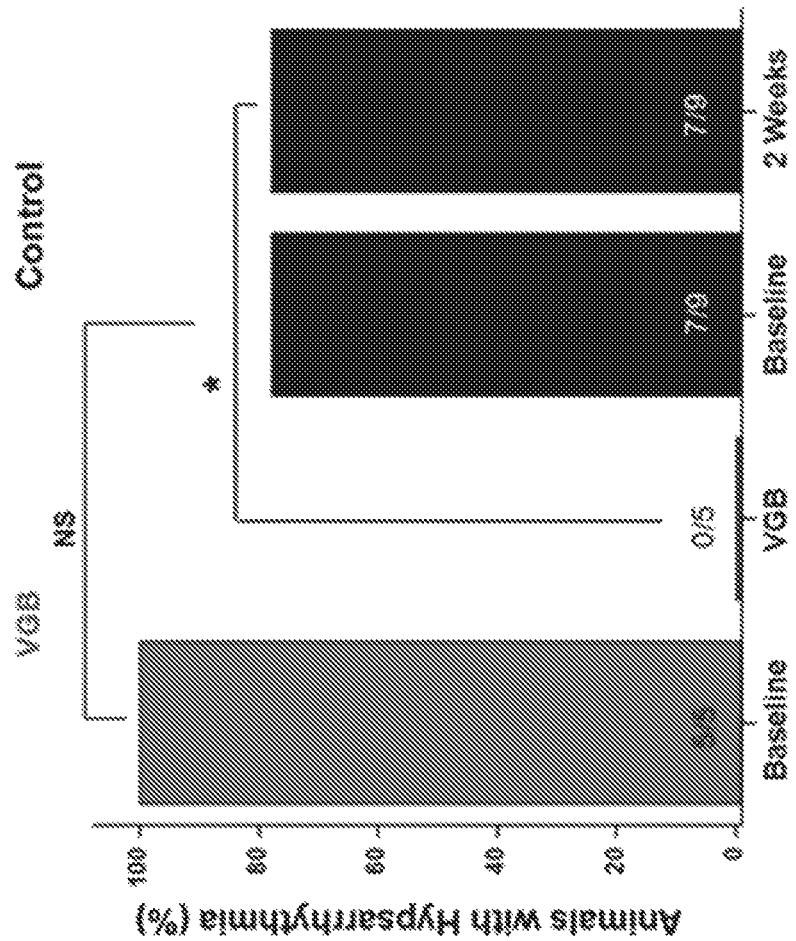
Figure 14C:
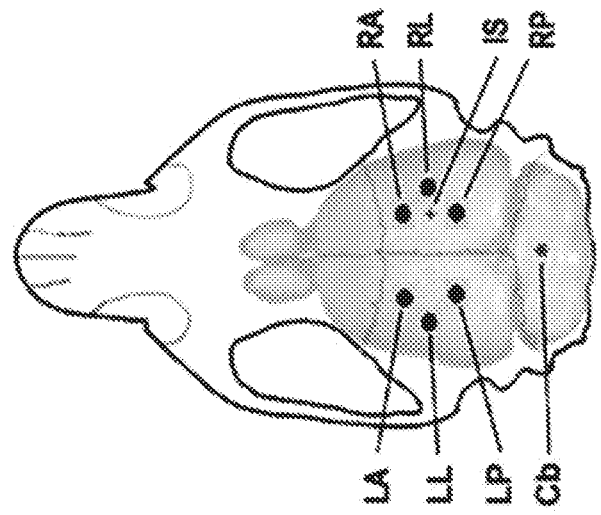

FIG. 14C comprises a diagram showing the electrode placement for the EEG recordings shown in FIGS. 14A-14B.

FIG. 14D comprise a graph illustrating effects of VGB treatment on hypsarrhythmia in a group of 5 rats in which this abnormal EEG pattern was present at baseline and was eliminated in all of them after treatment. In the control group, 7 of 9 animals had hypsarrhythmia at baseline and all of them continued to have it after treatment with the vehicle for the drug.

Figure 15A:
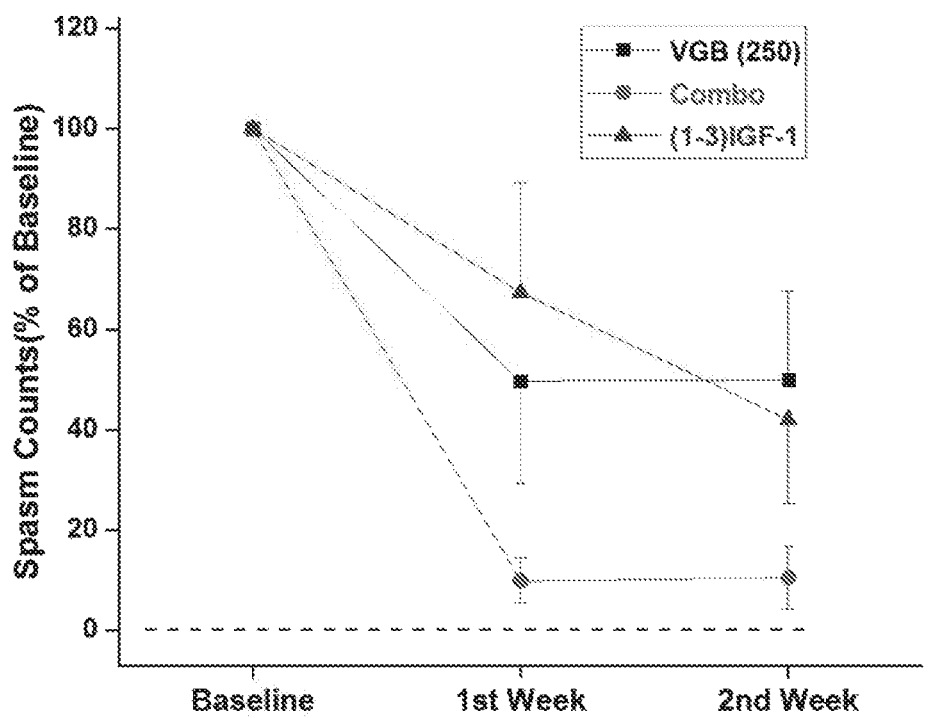
Figure 15B:
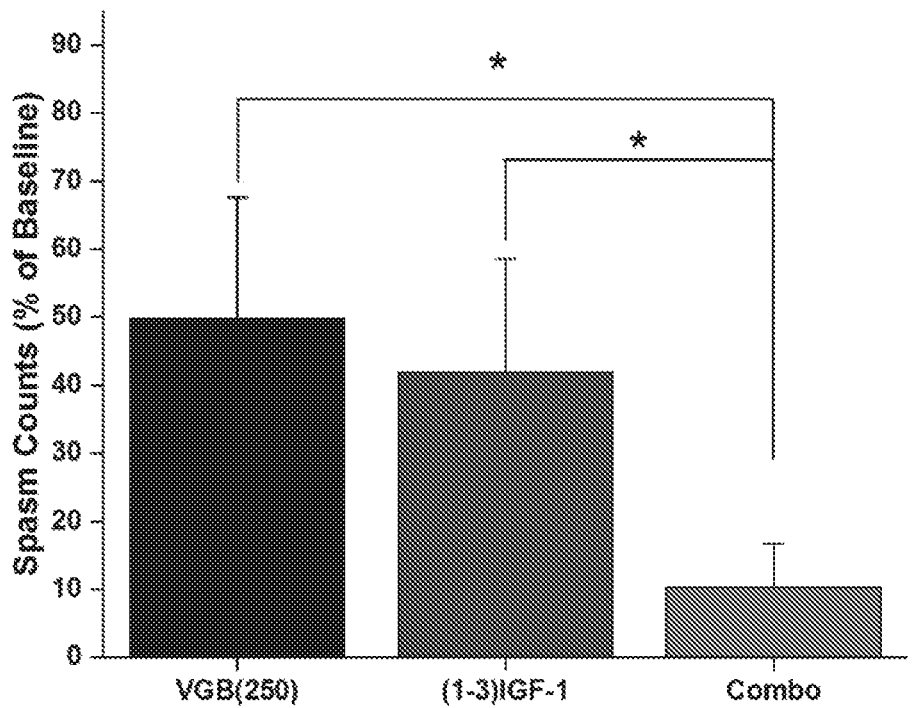

FIGS. 15A-15B comprise graphs reporting spasm reducing effect of IGF-1 alone, VGB alone and a combination treatment of IGF-1 and VGB together. FIG. 15A reports spasm counts at start, 1 week and 2 weeks for subjects where: VGB was injected daily at 250 mg/kg/day (i.p.); (1-3)IGF-1 was given daily at 10 mg/kg/day; or both were administered simultaneously. When the same dosages of the drug were given simultaneously to subjects (Combo), a very rapid and dramatic reduction in spasms was observed. FIG. 15A plots the daily spasm counts averaged at weekly intervals and normalized to the baseline spasm counts in each subject. FIG. 15B comprises a bar graph that plots the changes in spasm counts at the 2 week time point in FIG. 15A.

Figure 16A:
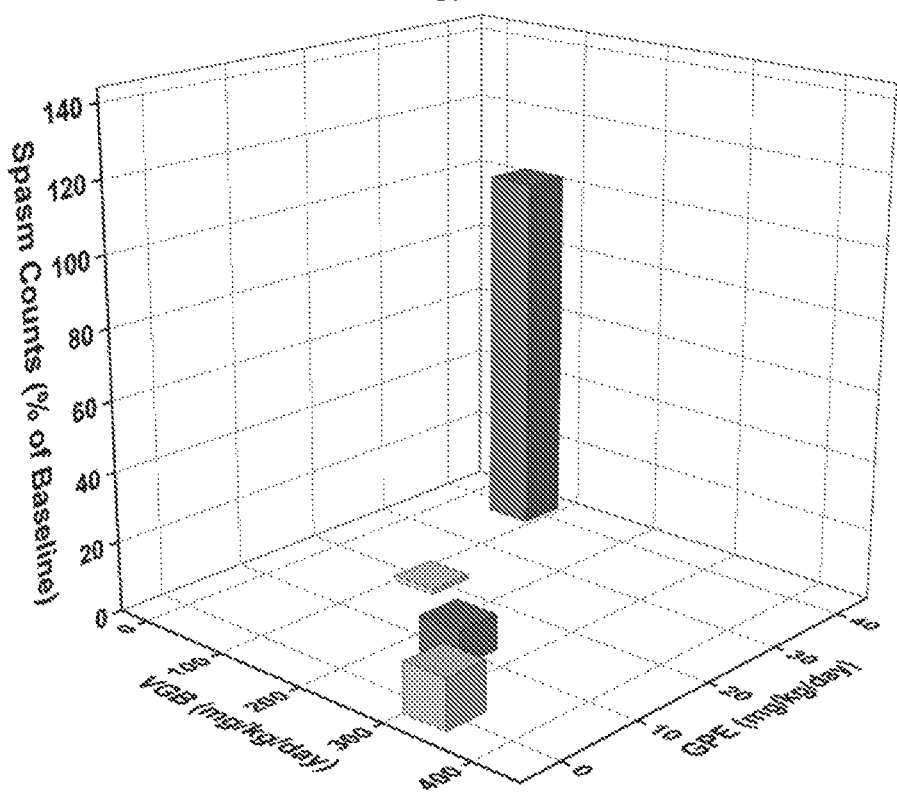
Figure 16B:
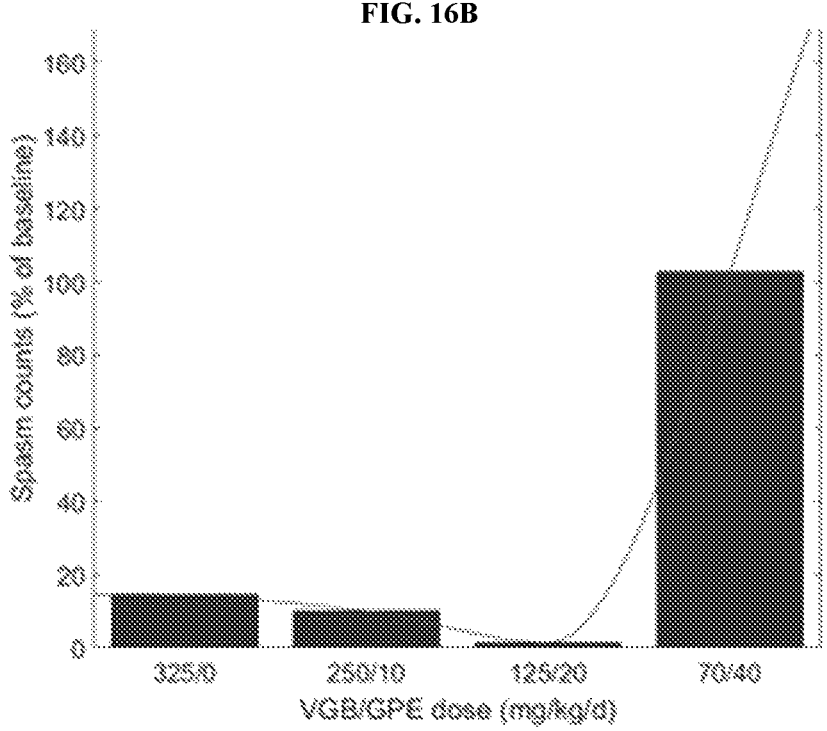

FIGS. 16A-16B comprise graphs reporting spasm reducing effect of different ratios of IGF-1 and VGB when given together as combination therapies. Spasm counts are normalized to baseline counts in each subject. Treatment was for 2 weeks at each combination dosages. As the VGB dosage was reduced and (1-3)IGF-1 dosage increased, the anticonvulsant effects were maintained or possibly increased until a VGB dosage of 70 mg/kg/day and 40 mg/kg/day of (1-3)IGF-1 was tested and spasm suppression no longer occurred.

Figure 17:
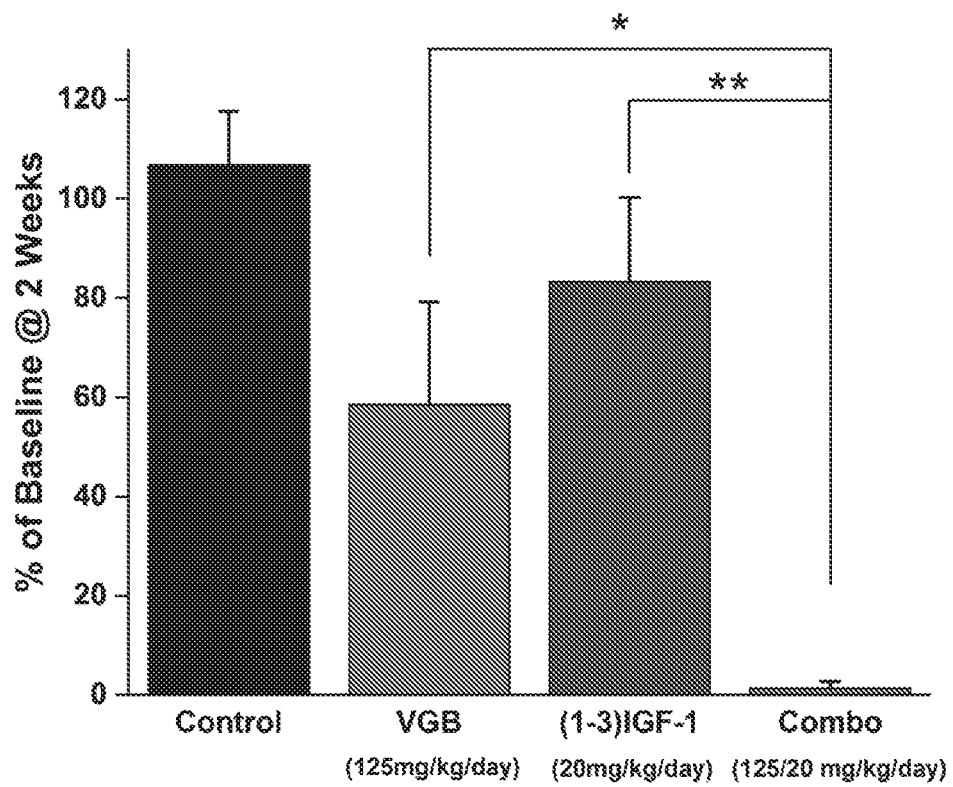

FIG. 17 comprises a graph comparing effects of VGB (125 mg/kg/day), (1-3)IGF-1 (20 mg/kg/day) and the combination of the 2 drugs at these dosages. Plotted are daily spasm counts at the end of the second week of treatment. Spasm counts were normalized to baseline counts in each subject.

FIGS. 18A-18C comprise bar graphs illustrating spasm counts obtained for rats treated with vigabatrin only (FIG. 18A) and certain combinations of vigabatrin and (1-3)IGF-1 (FIGS. 18B-18C). Comparisons are also made to the effects of the same dosages of (1-3) IGF-1 and vigabatrin alone.

Figure 19C:
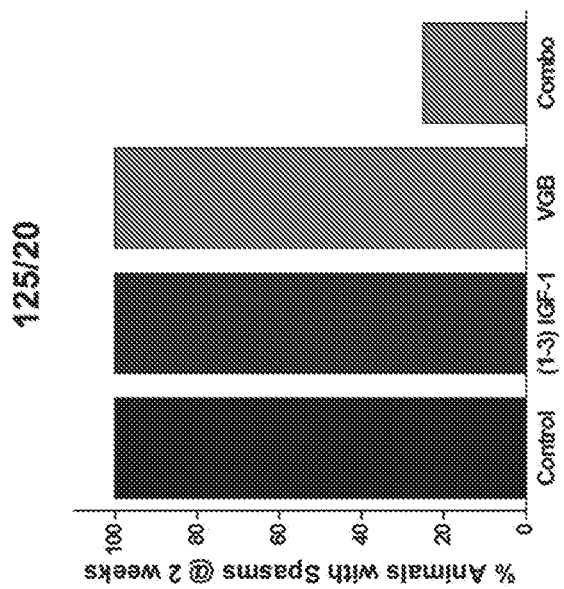
Figure 19B:
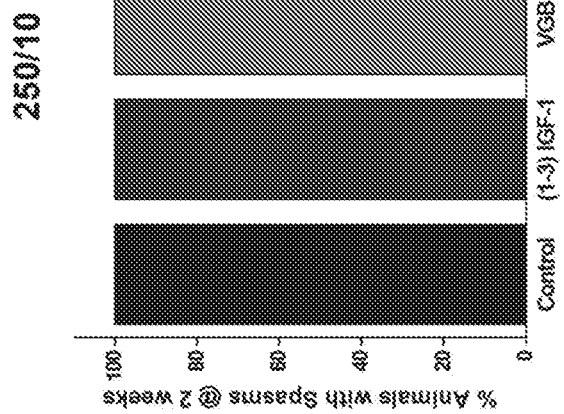
Figure 19A:
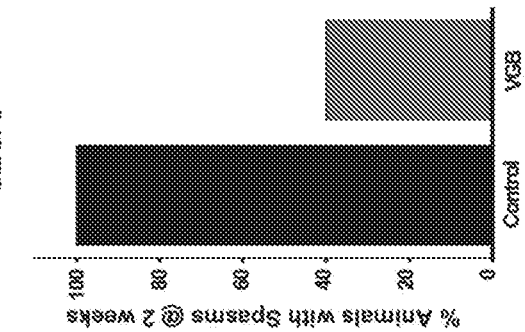

FIGS. 19A-19C comprise bar graphs illustrating % animals with spasms, as observed for rats treated with vigabatrin only (FIG. 18A) and certain combinations of vigabatrin and (1-3)IGF-1 (FIGS. 18B-18C). Comparisons are also made to the effects of the same dosages of (1-3) IGF-1 and vigabatrin alone.

Figure 20A:
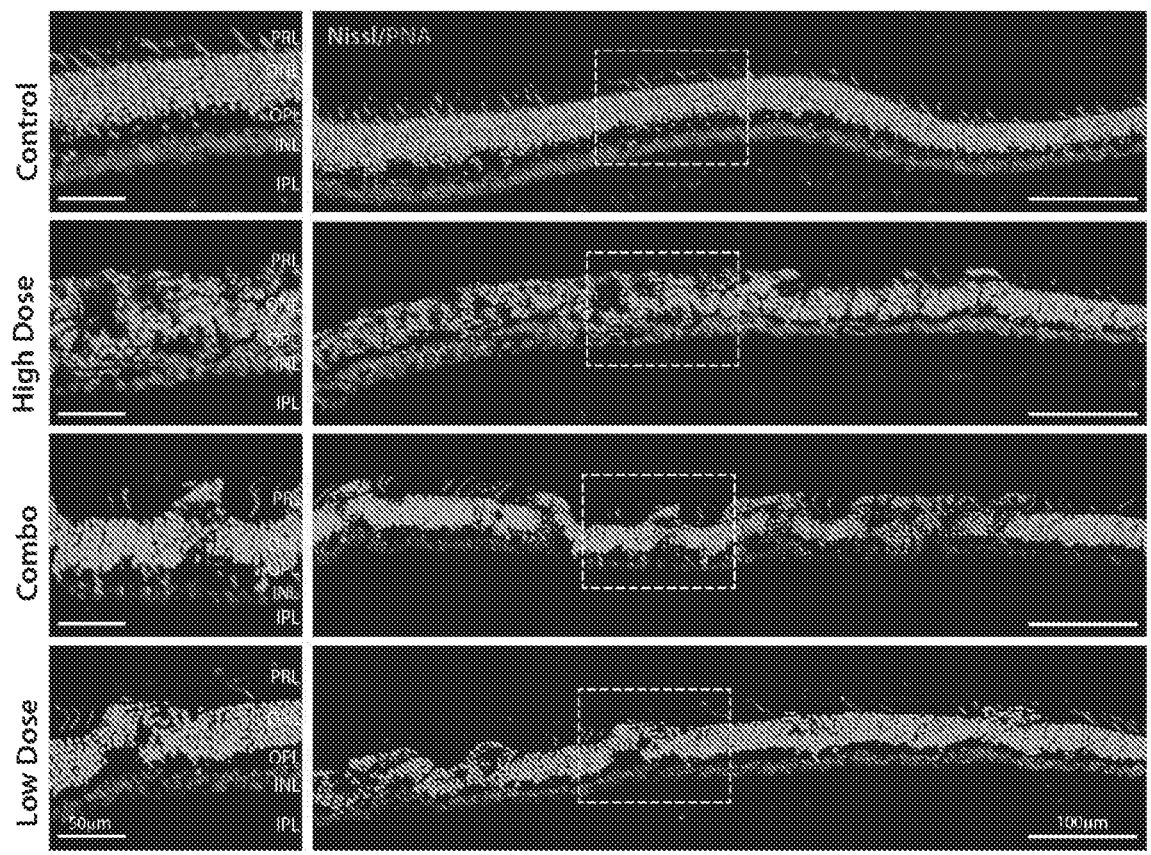
Figure 20B:
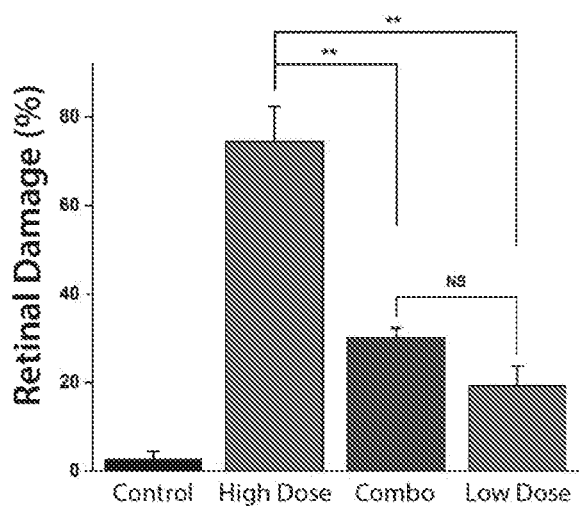
Figure 20C:
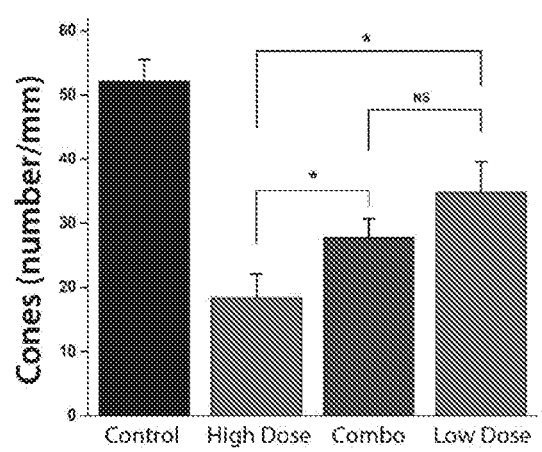

FIGS. 20A-20C illustrate results obtained in studies comparing retinotoxicity in rats treated with vigabatrin as the single therapeutic agent, or a combination of vigabatrin and (1-3)IGF-1. Photoreceptors were severely damaged by high-dose vigabatrin, and much less so by the combination therapy. FIG. 20A illustrates effects of high-dose vigabatrin and combination therapy on integrity of retinal cell layers. FIG. 20B comprises a bar graph illustrating retinal damage, as determined by quantifying length of the retina with discernible photoreceptor layer damage and expressing it as % total retinal length. FIG. 20C comprises a bar graph illustrating retinal damage, as determined by counting cone photoreceptors.

Figure 21:
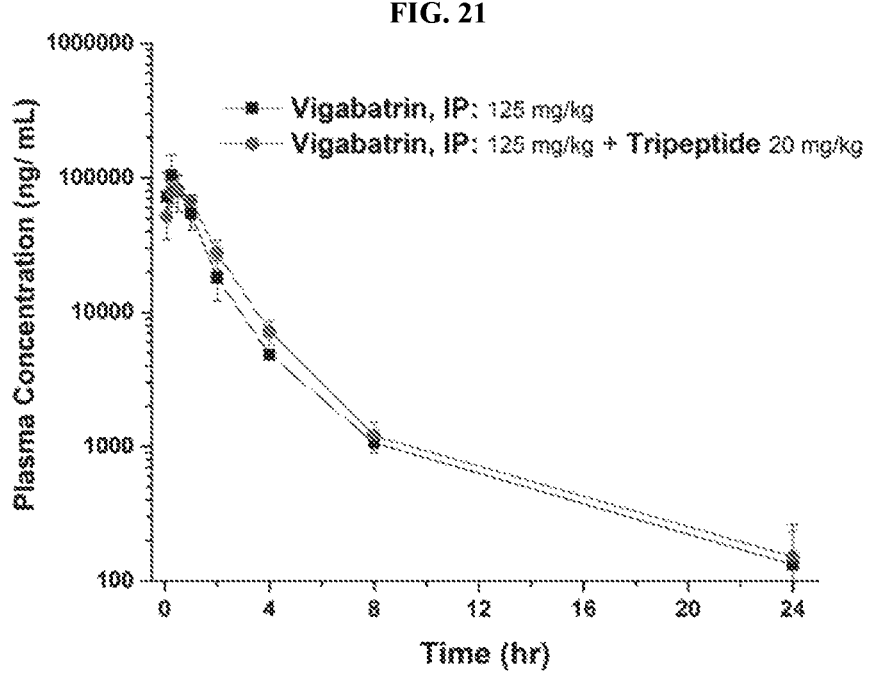
Figure 22A:
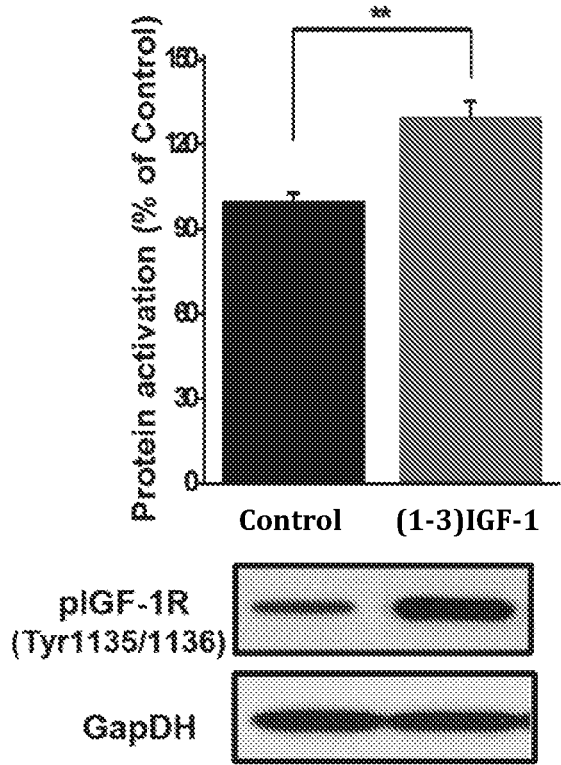
Figure 22B:
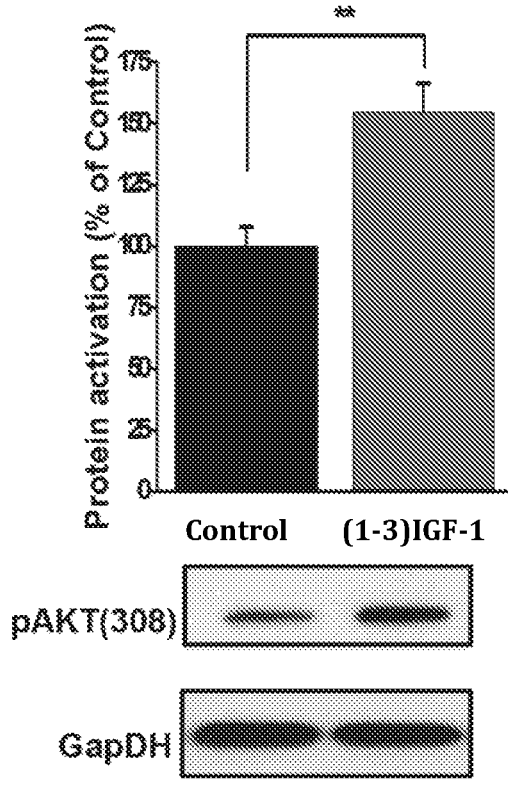
Figure 22C:
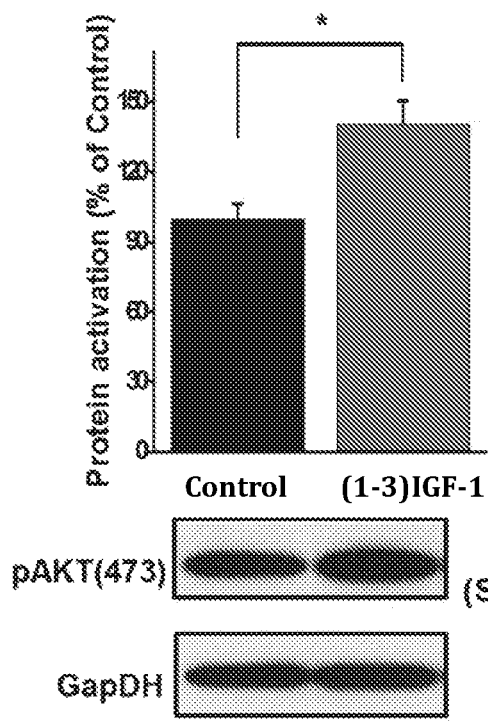
Figure 22D:
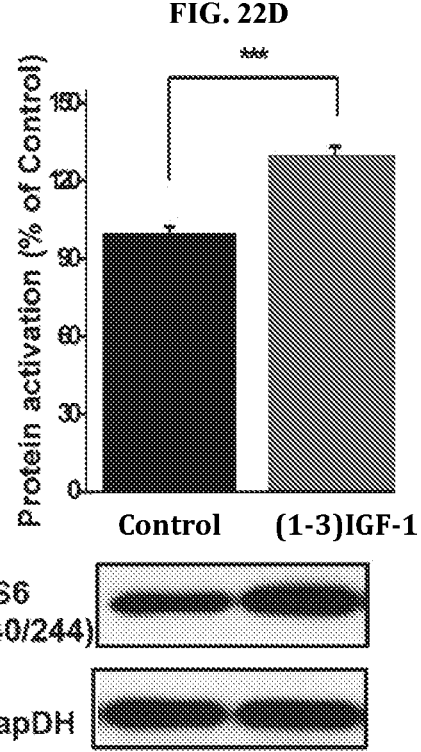
Figure 22E:
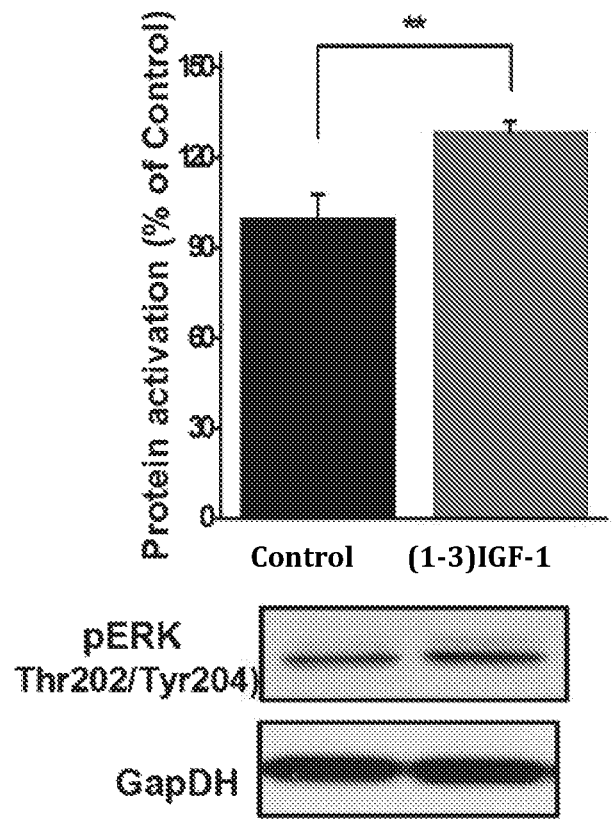

FIG. 21 comprises a graph illustrating plasma concentration for vigabatrin (administered to rats at 125 mg/kg) when administered alone or in combination with (1-3)IGF-1 (20 mg/kg). Co-administration of (1-3)IGF-1 had no discernible effect on vigabatrin pharmacokinetics.

FIGS. 22A-22E illustrate the finding that (1-3)IGF-1 engages the IGF-1R-PI3K-AKT and IGF-1R-Ras-ERK signaling cascades in neocortex. The experiments were performed using N=5 for both control and epileptic groups. Animals were 6 weeks old and sacrificed 2 hours after treatment.

Figure 23A:
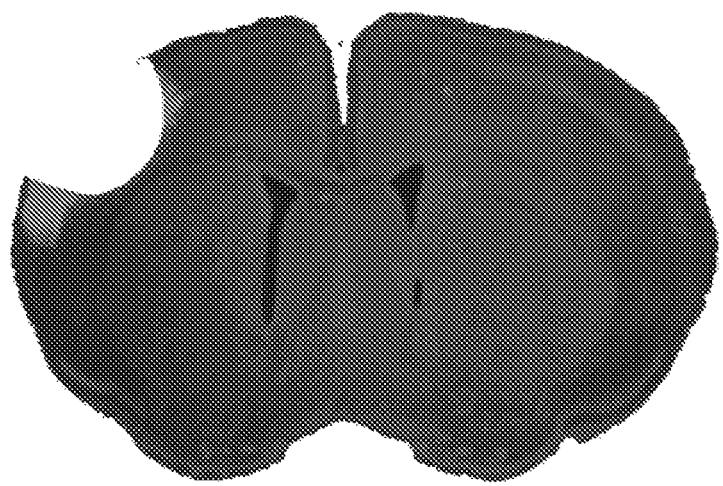
Figure 23B:
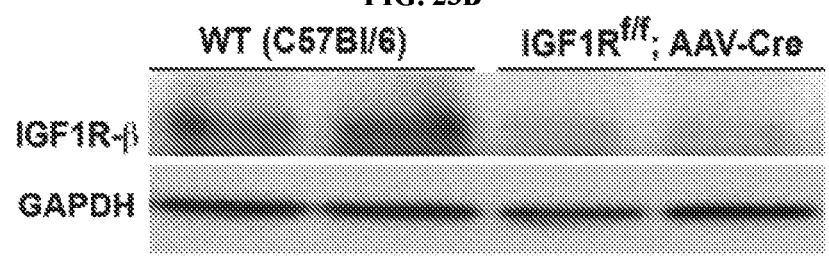
Figure 23C:
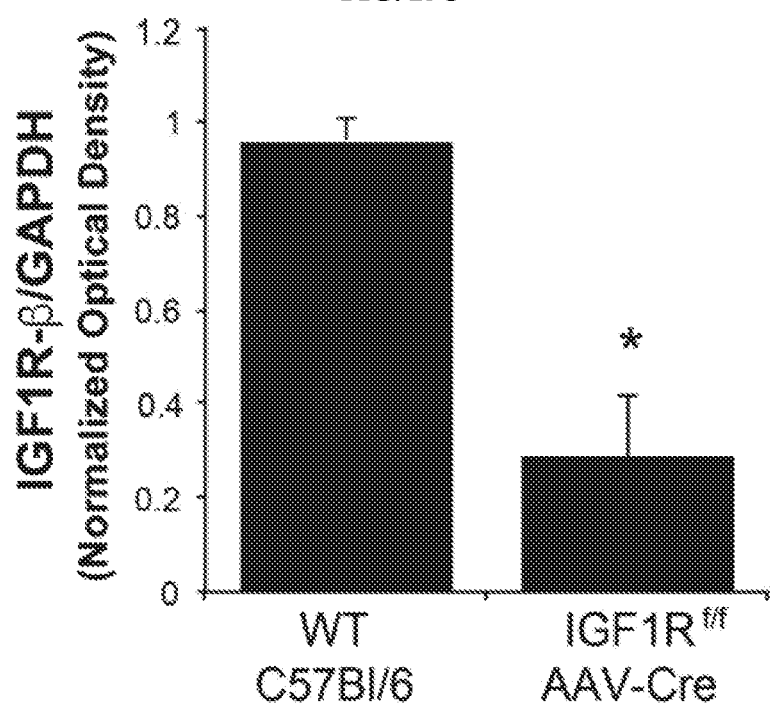

FIGS. 23A-23D illustrate the finding that (1-3)IGF-1 acts through IGF-1R. The neocortex of IGF-1R$^{f/f}$ mice was injected with AAV-Cre virus on P1. Using dTomato as reporter, tissue punches were taken from transfected region on P25 (FIG. 23A). Western blots show a >75% reduction in IGF-1R (FIGS. 23B-23C). Transfected mice and controls were treated with (1-3)IGF-1 or vehicle on P25. Tissue punches were taken 2 hours later, and it was found that elimination of IGF-1R prevented AKT phosphorylation (FIG. 23D).

Figure 24:
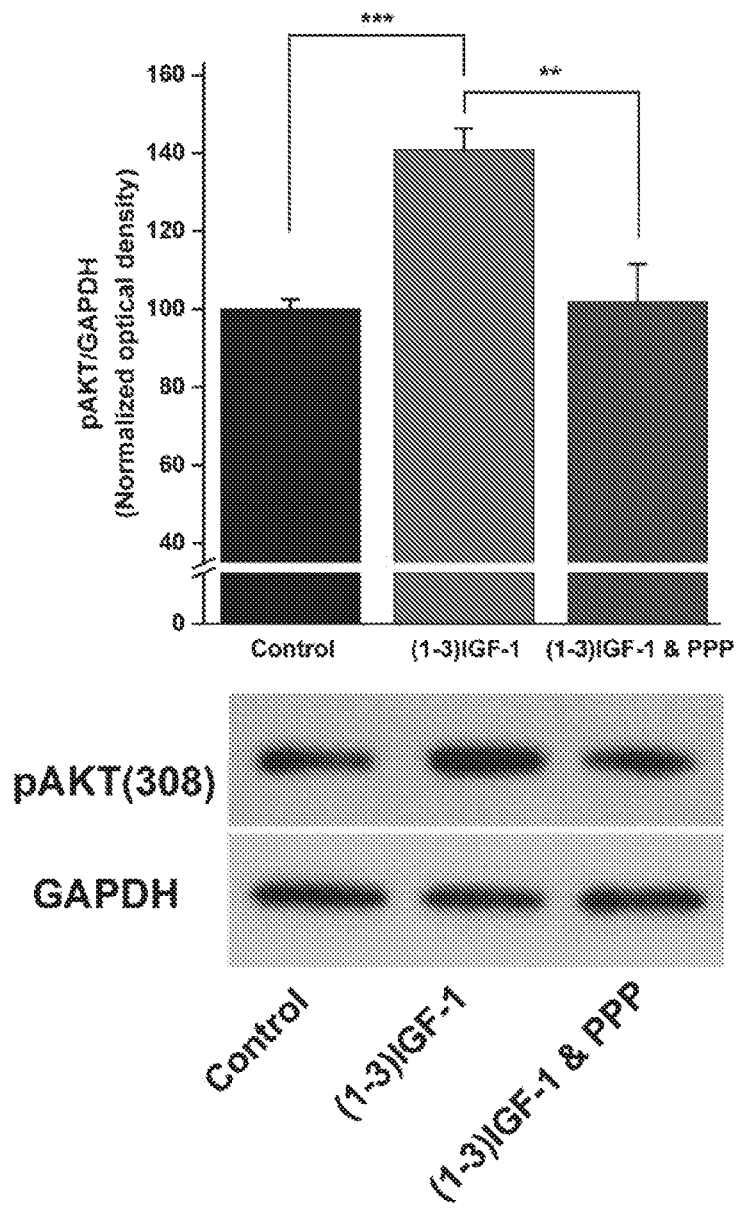

FIG. 24 is a bar graph illustrating the finding that the selective IGF-1R antagonist, picropodophyllin (PPP) blocks (1-3)IGF-1 induced activation of AKT. Animals (6 weeks old) were treated with 50 mg/kg of PPP or DMSO vehicle. Four hours later, they received 20 mg/kg of (1-3)IGF-1 or vehicle. Two hour later the neocortex was collected.

Figure 25A:
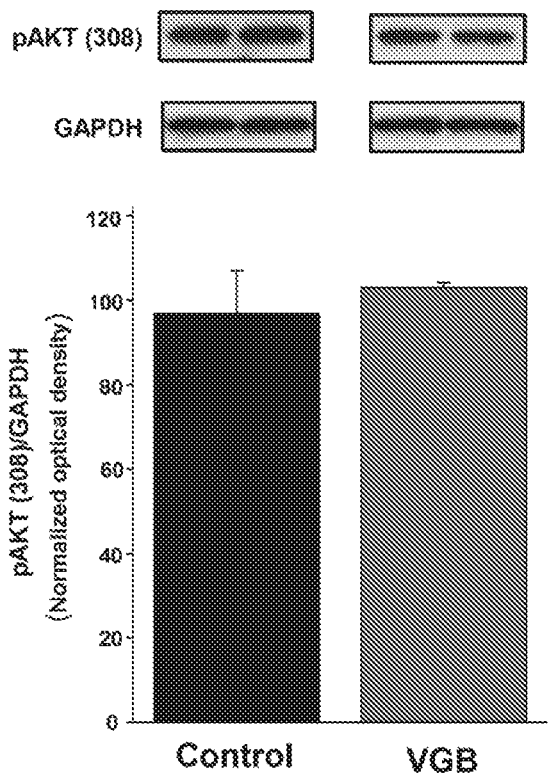
Figure 25B:
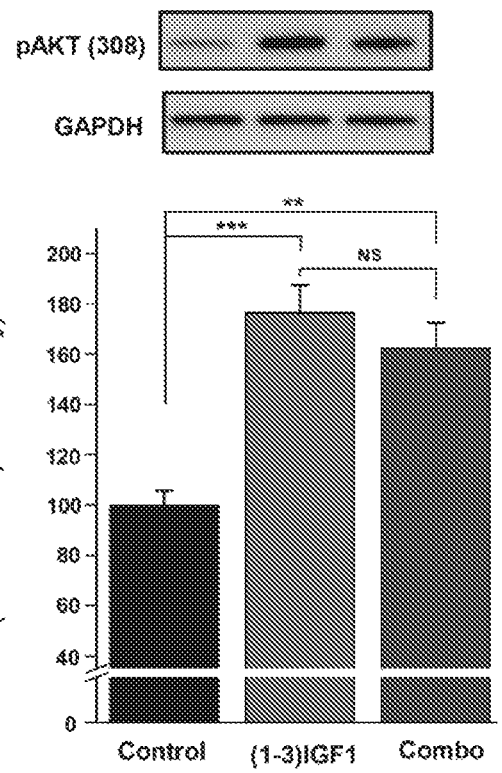

FIGS. 25A-25B illustrate the finding that vigabatrin does not activate IGF-1R signaling, and it does not alter (1-3) IGF-1-induced IGF-1R signaling. Vigabatrin (125 mg/kg) was injected 2 and 24 hours before collecting neocortex. In upper panel, western blots from 2 animals and controls were obtained (FIG. 25A) for bar graph n=6. For the combination study, the animals were administered vigabatrin (125/mg/kg), and (1-3)IGF-1 (20 mg/kg) was injected 30 min before collecting cortex in the combination group and the (1-3) IGF-1-only group. Controls received vehicle only. The results are illustrated in FIG. 25B.

Figure 26:
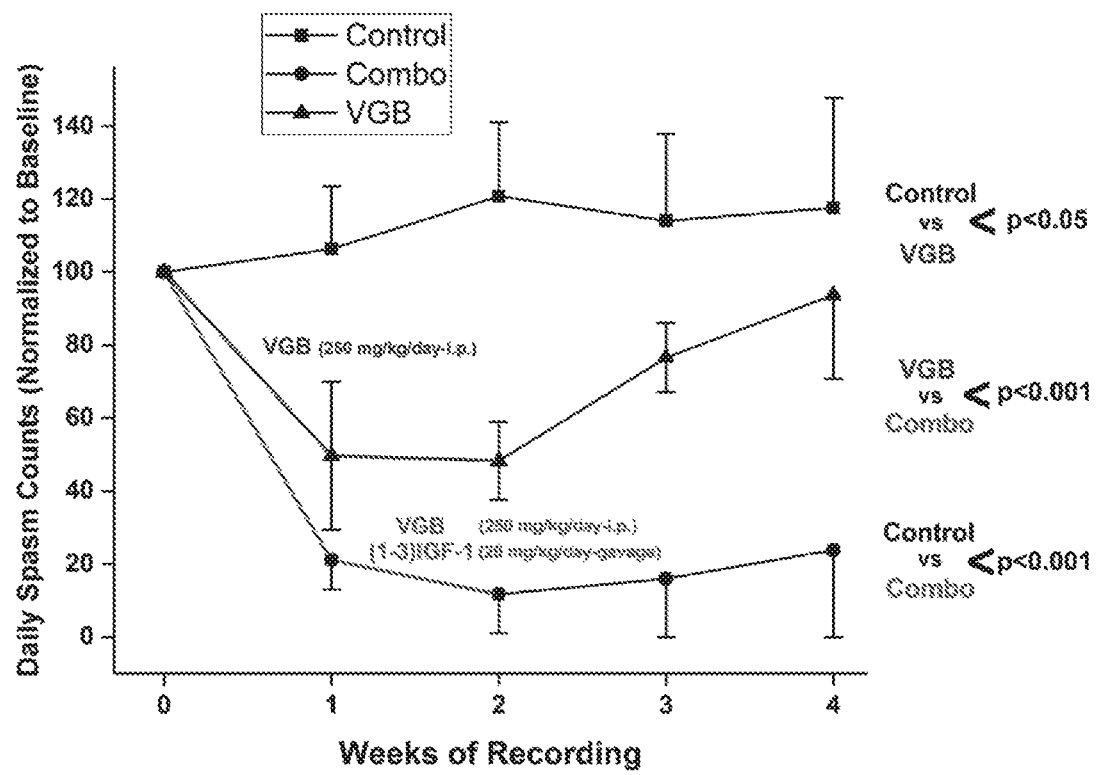

FIG. 26 is a graph illustrating the finding that, when (1-3)IGF-1 is administered orally and in combination with vigabatrin (i.p.), the effects on spasms counts were greater than when giving vigabatrin alone.

DETAILED DESCRIPTION OF THE INVENTION

The present invention provides methods of treating infantile spasms in a subject in need thereof. In certain embodiments, the subject suffers from catastrophic childhood epilepsy. In other embodiments, the method comprises administering to the subject both vigabatrin (VGB) and an insulin-like growth factor 1 (IGF-1) agent, which can be IGF-1 itself, a biologically active fragment thereof, such as, but not limited to, des(1-3)IGF-1, Gly-Pro-Glu (also known as (1-3)IGF-1), and/or cyclic prolylglycine, or any salt, solvate, enantiomer or derivative thereof. In other embodiments, the combination therapy of the invention has an unexpected synergistic effect, whereby the therapeutic effect of the combination of the two compounds is greater than the additive benefit of the two compounds combined. In yet other embodiments, the IGF-1 agent is co-administered with vigabatrin. In yet other embodiments, the IGF-1 agent is coformulated with vigabatrin. In yet other embodiments, the IGF-1 agent is co-administered with vigabatrin orally. In yet other embodiments, the IGF-1 agent is co-formulated with vigabatrin, and the co-formulation is administered orally. In yet other embodiments, the method comprises administering to the subject as the single anti-spasm therapeutic agent an insulin-like growth factor 1 (IGF-1) agent, which can be IGF-1 itself, a biologically active fragment thereof, such as, but not limited to, des(1-3)IGF-1, (1-3)IGF-1, and/or cyclic prolylglycine, or any salt, solvate, enantiomer or derivative thereof. In yet other embodiments, the subject is not administered vigabatrin.

Definitions

As used herein, each of the following terms has the meaning associated with it in this section.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

Generally, the nomenclature used herein and the laboratory procedures in the fields of neuroscience and pharmacology are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount" or "therapeutically effective amount" or "pharmaceutically effective amount" of a compound are used interchangeably to refer to the amount of the compound that is sufficient to provide a beneficial effect to the subject to which the compound is administered.

As used herein, the term "des(1-3)IGF-1" refers to a IGF-1 polypeptide corresponding to the full length IGF-1 lacking the N-terminal Gly-Pro-Glu tripeptide (also known as (1-3)IGF-1).

As used herein, the term "(1-3)IGF-1" refers to the N-terminal Gly-Pro-Glu peptide of IGF-1.

As used herein, the term "infantile spasms", also known as "juvenile spasms", "West syndrome" and "Generalized Flexion Epilepsy," is a disorder that primarily affects infants and generally manifests within the first year of life. Symptoms include spasms, which can be violent or subtle, as well as long term mental impairment.

As used herein, the term "hypsarrhythmia" is a highly abnormal "chaotic" EEG pattern prominently recorded during non-REM sleep in infantile spasms patients.

As used herein, the term "IGF-1" refers to insulin-like growth factor, which in humans has the following sequence (SEQ ID NO:1). The GPE tripeptide is shown in bold underlined: GPETL CGAEL VDALQ FVCGD RGFYF NKPTG YGSSS RRAPQ TGIVD ECCFR SCDLR RLEMY CAPLK PAKSA (SEQID NO:1)

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "pharmaceutical composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound include, but are not limited to, intravenous, oral, aerosol, parenteral, ophthalmic, pulmonary and topical administration.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease. Disease and disorder are used interchangeably herein.

As used herein, the term "prodrug" refers to a pharmacological substance, drug, formulation or compound that is administered to a subject in an inactive form. Once administered, the prodrug is metabolized in vivo into an active metabolite. In certain embodiments, a prodrug should undergo chemical conversion by metabolic processes before becoming an active pharmacological agent.

A "therapeutic" treatment is a treatment administered to a subject who exhibits signs of pathology for the purpose of diminishing or eliminating those signs.

"Treating," as used herein, means reducing the frequency with which symptoms are experienced by a patient or subject, or administering an agent or compound to reduce the severity with which symptoms are experienced by a patient or subject. An appropriate therapeutic amount in any individual case may be determined by one of ordinary skill in the art using routine experimentation.

As used herein, the term "vigabatrin" refers to the compound γ-vinyl-GABA having the structure:

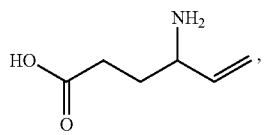

or a salt or solvate thereof.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 and so forth, as well as individual numbers within that range, for example, 1, 2, 2.7, 3, 4, 5, 5.3, and 6. This applies regardless of the breadth of the range.

The following abbreviations are used herein: ACTH, adrenocorticotropic hormone; cPG, cyclic prolylglycine; EEG, electroencephalogram; IGF-1, insulin-like growth factor 1; GPE, glycine-proline-glutamate; mg/kg/day; milligrams of compound per kilogram of body weight per day; VGB, vigabatrin.

Methods

The invention provides methods of treating treatment-resistant epilepsy in a subject in need thereof, the method comprising administering to the subject a therapeutically effective amount of vigabatrin, or a salt or solvate thereof, and administering to the subject a therapeutically effective amount of an IGF-1 agent, or a salt or solvate thereof.

In certain embodiments, the IGF-1 agent is IGF-1, a biologically active fragment thereof, such as, but not limited to, (1-3)IGF-1 (also known as GPE), des(1-3)IGF-1), or any derivative thereof. In other embodiments, the IGF-1 agent is des(1-3)IGF-1 or a salt, solvate or derivative thereof (such as, for example, a N-methylated derivative, an ester, an amide, or any combinations thereof). In yet other embodiments, the IGF-1 agent is (1-3)IGF-1 or a salt, solvate or derivative thereof (such as, for example, a N-methylated derivative, an ester, an amide, or any combinations thereof). In yet other embodiments, the IGF-1 agent is cyclic prolylglycine (also known as cyclic glycine-proline or cPG), or a salt, enantiomer, solvate or derivative thereof.

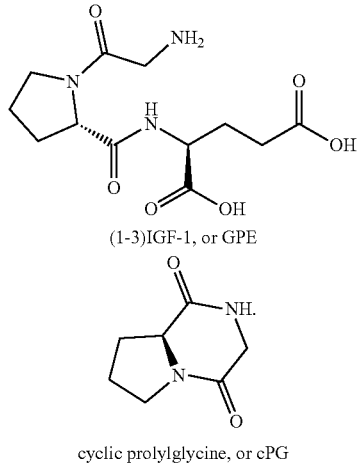

In certain embodiments, the N-methylated derivative of the IGF-1 agent is methylated in one or more of the amide groups of the IGF-1 agent. In other embodiments, the derivative of the IGF-1 agent is the amide derivative of the C-terminus acid (or any internal acid residue) of the IGF-1 agent. In yet other embodiments, the IGF-1 agent is the $C_1$-$C_6$ ester of the C-terminus acid (or any internal acid residue) of the IGF-1 agent.

In certain embodiments, vigabatrin and the IGF-1 agent are administered to the subject simultaneously. In other embodiments, vigabatrin is administered to the subject before the IGF-1 agent. In other embodiments, the IGF-1 agent is administered to the subject before vigabatrin. In yet other embodiments, vigabatrin and the IGF-1 agent are co-formulated.

In certain embodiments, vigabatrin is administered in a dosage ranging from about 50 mg/kg/day to about 400 mg/kg/day. In other embodiments, vigabatrin is administered in a dosage ranging from about 100 mg/kg/day to about 250 mg/kg/day. In yet other embodiments, vigabatrin is administered in a dosage of about 125 mg/kg/day.

In certain embodiments, the IGF-1 agent is administered in a dosage ranging from about 1 mg/kg/day to about 200 mg/kg/day. In other embodiments, the IGF-1 agent is administered in a dosage of about 10 mg/kg/day to about 50 mg/kg/day. In yet other embodiments, the IGF-1 agent is administered in a dosage of about 20 mg/kg/day. In certain embodiments, IGF-1 is administered in a dosage of about 1 mg/kg/day. In other embodiments, (1-3)IGF-1 is administered in a dosage of about 10 mg/kg/day to about 50 mg/kg/day.

In certain embodiments, methods of the invention can be used to treat one or more treatment-resistant epilepsy causing disorders selected from the group consisting of infantile spasms, refractory complex partial epilepsy, secondary generalized seizures, temporal lobe epilepsy, simple partial seizures, and refractory seizures.

In certain embodiments, (1-3)IGF-1 is effective in treating treatment-resistant epilepsy. In certain embodiments, (1-3)IGF-1 is effective in treating infantile spasms. In certain embodiments, the invention provides methods of treating infantile spasms in a subject in need thereof, the method comprising administering to the subject a therapeutically effective amount of vigabatrin, or a salt or solvate thereof, and administering to the subject a therapeutically effective amount of (1-3)IGF-1, or a salt, solvate, or derivative thereof.

In certain embodiments, des(1-3)IGF-1 is effective in treating treatment-resistant epilepsy causing disorders. In certain embodiments, des(1-3)IGF-1 is effective in treating infantile spasms. In certain embodiments, the invention provides methods of treating infantile spasms in a subject in need thereof, the method comprising administering to the subject a therapeutically effective amount of vigabatrin, or a salt or solvate thereof, and administering to the subject a therapeutically effective amount of des(1-3)IGF-1, or a salt, solvate, or derivative thereof.

In certain embodiments, cPG is effective in treating treatment-resistant epilepsy causing disorders. In certain embodiments, cPG is effective in treating infantile spasms. In certain embodiments, the invention provides methods of treating infantile spasms in a subject in need thereof, the method comprising administering to the subject a therapeutically effective amount of vigabatrin, or a salt or solvate thereof, and administering to the subject a therapeutically effective amount of cPG, or a salt, solvate, or derivative thereof.

In certain embodiments, the combined administration of the IGF-1 agent and vigabatrin reduces spasm occurrence by more than about 90% in the subject. In other embodiments, the combined administration of the IGF-1 agent and vigabatrin reduces spasm occurrence by more than about 95% in the subject. In other embodiments, the combined administration of the IGF-1 agent and vigabatrin reduces spasm occurrence by about 100% in the subject.

In certain embodiments, the combined administration of both the IGF-1 agent and vigabatrin exhibits an unexpected synergistic effect in treating infantile spasms, wherein the combined treatment has a greater than additive effect than the two treatments individually. In other embodiments, the combined administration allows for a lower therapeutically effective dose of vigabatrin to be used than is normally administered, thereby reducing the likelihood or severity of potential side effects. In certain embodiments, the combination therapy reduces the likelihood and/or severity of one or more potential side effects selected from the group consisting of retinotoxicity, neurotoxicity, peripheral neuropathy, renal complications, drowsiness, headache, dizziness, anxiety, depression, memory loss, impairment of cognitive development, diplopia, aggression, ataxia, vertigo, hyperactivity, vision loss, retinal nerve fiber damage, confusion, insomnia, impaired concentration, speech disorders, irritability, tremors, emotional lability, and abnormal gait.

In certain embodiments, at least one of the compounds is formulated as part of an extended-release formulation. In other embodiments, at least one of the compounds is administered to the subject by at least one route selected from the group consisting of inhalational, oral, rectal, vaginal, parenteral, topical, transdermal, pulmonary, intranasal, buccal, sublingual, ophthalmic, intrathecal, intravenous and intragastrical.

In certain embodiments, the subject is a mammal. In other embodiments, the subject is a human.

Combination Therapies

In certain embodiments, the compounds of the present invention are useful in the methods of present invention in combination with one or more additional compounds useful for treating the diseases or disorders contemplated within the invention. These additional compounds may comprise compounds of the present invention or compounds, e.g., commercially available compounds, known to treat, prevent, or reduce the symptoms of the diseases or disorders contemplated within the invention.

The methods of the present invention can be used in combination with other treatment regimens, including anti-epileptic compounds. In certain embodiments, the methods of the invention can be used in combination with administration of adrenocorticotropic hormone (ACTH). In other embodiments, the methods of the invention can be used in combination with administration of prednisolone. In yet other embodiments, the methods of the invention can be used in combination with administration of any drug or treatment regimen known in the art to treat intractable forms of epilepsy. In certain embodiments, the methods of the invention can be used in combination with administration of carbamazepine, clonazepam, felbamate, gabapentin, lacosamide, lamotrigine, levetiracetam, oxcarbazine, phenobarbital, phenytoin, pregabalin, primidone, tiagabine, topiramate, valproate, and zonisamide. The compounds of the present invention may be administered before, during, after, or throughout administration of any therapeutic agents used in the treatment of a subject's disease or disorder.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions useful within the present invention to a patient, preferably a mammal, more preferably a human, may be carried out using known procedures, at dosages and for periods of time effective to treat a disease or disorder in the patient. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the present invention is from about 1 and 5,000 mg/kg of body weight/per day. One of ordinary skill in the art is able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the present invention employed in the pharmaceutical composition at levels lower than that required in order to achieve the desired therapeutic effect and gradually increase the dosage until the desired effect is achieved.

In particular embodiments, it is advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the present invention are dictated by and directly dependent on the unique characteristics of the therapeutic compound and the particular therapeutic effect to be achieved, and the limitations inherent in the art of compounding/formulating such a therapeutic compound for the treatment of a disease or disorder in a patient.

In certain embodiments, the compositions useful within the invention are formulated using one or more pharmaceutically acceptable excipients or carriers. In certain embodiments, the pharmaceutical compositions of the present invention comprise a therapeutically effective amount of a compound useful within the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions useful within the invention are administered to the patient in dosages that range from one to five times per day or more. In other embodiments, the compositions useful within the invention are administered to the patient in range of dosages that include, but are not limited to, once every day, every two, days, every three days to once a week, and once every two weeks. It is readily apparent to one skilled in the art that the frequency of administration of the various combination compositions useful within the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments thereinbetween.

In some embodiments, the dose of a compound is from about 1 mg and about 2,500 mg. In some embodiments, a dose of a compound of the present invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating a disease or disorder) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the present invention, alone or in combination with a second pharmaceutical agent; and instructions for using the compound to treat, prevent, or reduce one or more symptoms of a disease or disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other cognition improving agents.

The term "container" includes any receptacle for holding the pharmaceutical composition. For example, in certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Routes of administration of any of the compositions of the present invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

The present invention also includes a multi-layer tablet comprising a layer providing for the delayed release of one or more compounds of the present invention, and a further layer providing for the immediate release of a medication for treatment of a disease or disorder. Using a wax/pH-sensitive polymer mix, a gastric insoluble composition may be obtained in which the active ingredient is entrapped, ensuring its delayed release.

Parenteral Administration

For parenteral administration, the compounds may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the present invention may be administered in the form of microparticles, for example, by injection or in the form of wafers or discs by implantation.

In certain embodiments, the compounds of the present invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound depends on the age, sex and weight of the patient, the current medical condition of the patient and the progression of the disease or disorder in the patient being treated. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

The compounds for use in the method of the present invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction and/or treatment conditions with art-recognized alternatives and using no more than routine experimentation, are within the scope of the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Treatment with TTX (Tetrodotoxin)

11 or 12 day-old male or female rat pups were anesthetized with ketamine/xylazine and an osmotic mini pump (Alzet Model 2004) was implanted under the skin along the animals back. The day before implantation, the minipump was filled with 200 µL of 12 µM TTX, which was dissolved in phosphate buffered saline. Control rats were implanted with osmotic minipumps that contained only the vehicle. Pumps were connected to a 28 gauge stainless steel cannula (Plastics One 3280P-SPC) that was stereotaxically implanted into the right somatosensory cortex (AP: 2.2, ML: 2.0 from bregma and 0.8 mm below the surface of cortex) and anchored with dental acrylic. The pumps constantly infused TTX into the cortex over a 28 day period.

Drug Treatment

VGB was purchased from Sigma/Aldrich, (1-3)IGF-1 from Bachem, rhIGF-1 from Peprotech. Cyclic glycine-proline is available from Sigma-Aldrich. All drugs were dissolved in saline and a BSA carrier was added to peptide solutions to prevent loss on plastic and glass surfaces. All drugs were administered i.p. and given at daily intervals for 2 or 3 weeks depending on the experiment. In a few experiments, a single dose of (1-3)IGF-1 was given and the brains collected 1 hour later for analysis.

Video/EEG Recordings

In the TTX model, behavioral spasms are first observed between postnatal day (P) 16 and 20. Over time, spasm frequency increases and persists for several months. Thus EEG electrodes were implanted after weaning, usually between P27 to P35. On the following day, video/EEG recordings were initiated, and following 5 days of baseline recordings drug treatment was initiated. Video/EEGs were recorded continuously 24 hours/day, 7 days/week. Animals were housed individually in large, autoclavable Plexiglas recording cages and had free access to food and water throughout this time. The floor of the cages was constructed from stainless steel wire mesh (McMaster Carr) and the ceiling from Plexiglas that was designed to allow free passage of the cable (Plastics One: 363/2-000) from the rat headpost to a Plastics One commutator (SL12C/5B) mounted above each cage. This commutator allowed unhindered movement of animals within the cage. Wires from the commutator were fed to the head board of a Nicolet/Viasys instrument. The behavior of each animal was captured with a separate black and white camera (Supercircuit PC88WR) mounted just outside the recording cage and streamed to a Nicolet/Viasys instrument via a video splitter (Supercircuit QS22).

Recording electrodes were constructed from Teflon-coated stainless steel wire (0.005 inches in diameter –127 µm in bare diameter). Teflon was stripped 0.3-0.5 mm from the wire's tip. Recording electrodes were implanted 0.8 mm below the cortical surface at 6 sites in neocortex (FIGS. 9C and 14C), most commonly three weeks after pump implantation. Reference electrodes were placed in the cerebellum and electrodes in neck musculature served as isolated system grounds. The recording sites were chosen in relation to the TTX infusion site. Three electrodes were placed ipsilateral to the infusion site 3 mm anterior, posterior and lateral to the cannula implantation site. These electrodes were denoted as right anterior (RA), right posterior (RP) and right lateral (RL). Three additional electrodes were placed homotopically in the contralateral cortex and were referred to as left anterior (LA), left posterior (LP) and left lateral (LL). Recordings made on the Nicolet/Viasys instrument used a digital sampling rate of 2048 Hz.

Immunohistochemistry

After perfusion with PBS and 4% paraformaldehyde, brains were fixed overnight in a 4% paraformaldehyde at 4° C. Coronal sections (50-100 µm thick) were cut with a vibratome. Immunohistochemistry for IGF-1, IGF-1R, Transferrin Receptor, Parvalbumin, Calretinin, Synaptotagmin2 was conducted on brain sections containing the somatosensory cortex. To accomplish this, fixed sections were rinsed twice in PBS and then once in PBS with 0.3% Triton X-100 (Sigma) at 1 h intervals. The slices were then incubated in a solution containing the primary antibody for 24 hours at 4° C. This solution consisted of PBS, 0.3% Triton X-100 and the primary mouse monoclonal antibody. After rinsing the sections three times in PBS, the tissue was then incubated for 2 hours with an appropriate secondary antibody dissolved in PBS. Brain sections were again rinsed three times in PBS, and all sections were dried, dehydrated, mounted on slides and glass coversliped. All immunohistochemical reactions in slices from experimental and control animals were done simultaneously under identical conditions.

Western Blotting

Briefly, brains were quickly removed from the skull under anesthesia and the cortex dissected free from adhering tissue. It was then snap frozen on dry ice and later homogenized by sonication. Protein concentrations were determined by the BCA assay. Equal quantities of protein (10 µg) from each sample were resolved by polyacrylamide gel electrophoresis. The primary antibodies used were against: pAKT Thr308, pAkt Ser473, pS6 Ser240/244, AKT, S6, IGF-1R. Secondary antibodies were conjugated to horseradish peroxidase and visualization of immunoreactive bands was produced by enhanced chemiluminescence and then exposed to Kodak Biomax film. After digitization, band intensity was quantified with Image J Image software. Blots were also probed with antibodies to GAPDH, which served as a loading control. Band intensity was normalized to control values on the same blot.

Example 1: IGF-1 Reduction in Epileptic Neocortex

Figure 1A:
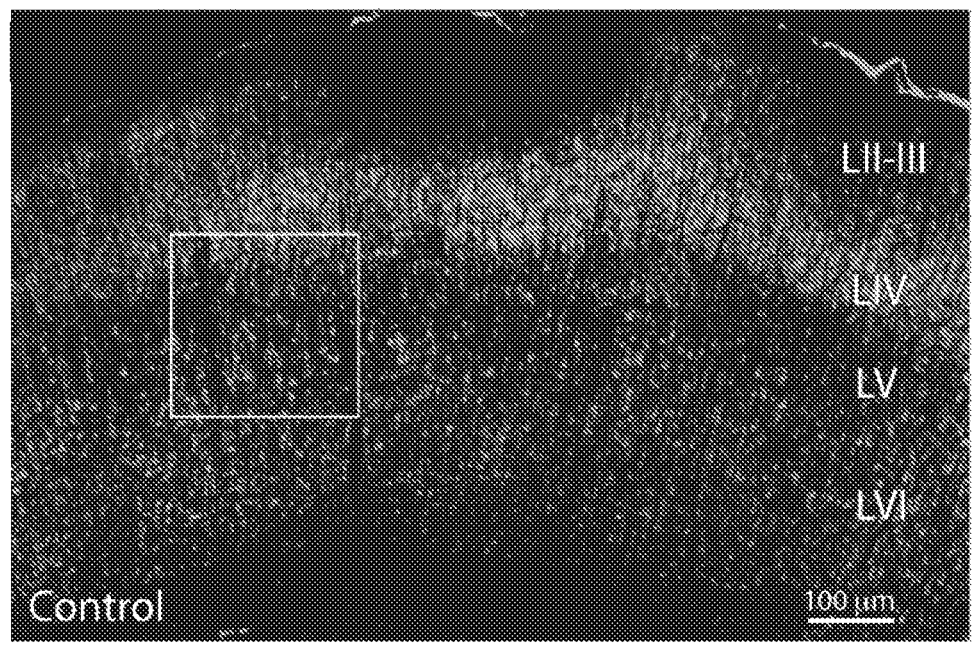
FIGS. 1A-1C comprise super resolution confocal images of immunostained coronal sections of the neocortex showing the lower prevalence of IGF-1 in the brain of an epileptic subject.
Figure 1B:
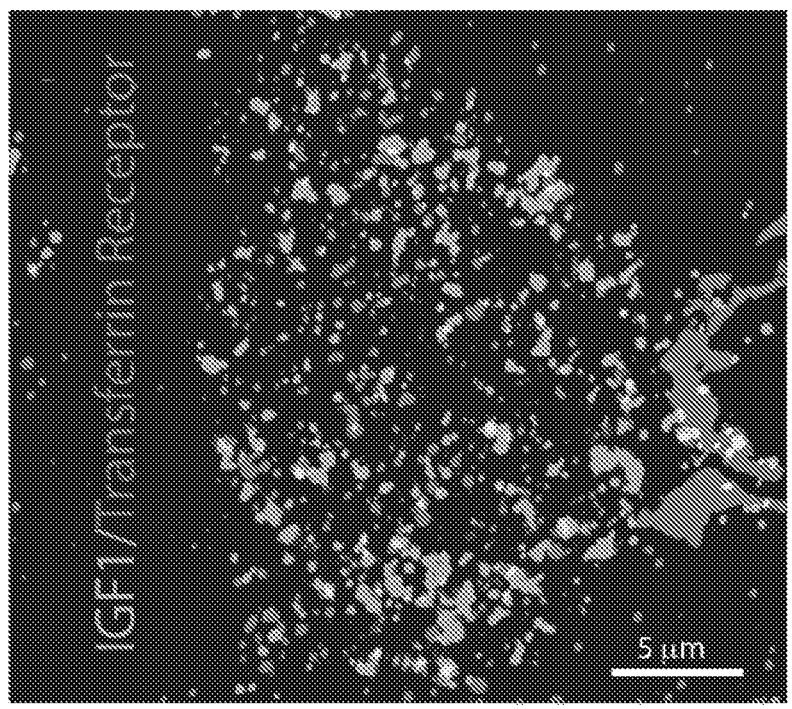
Figure 1C:
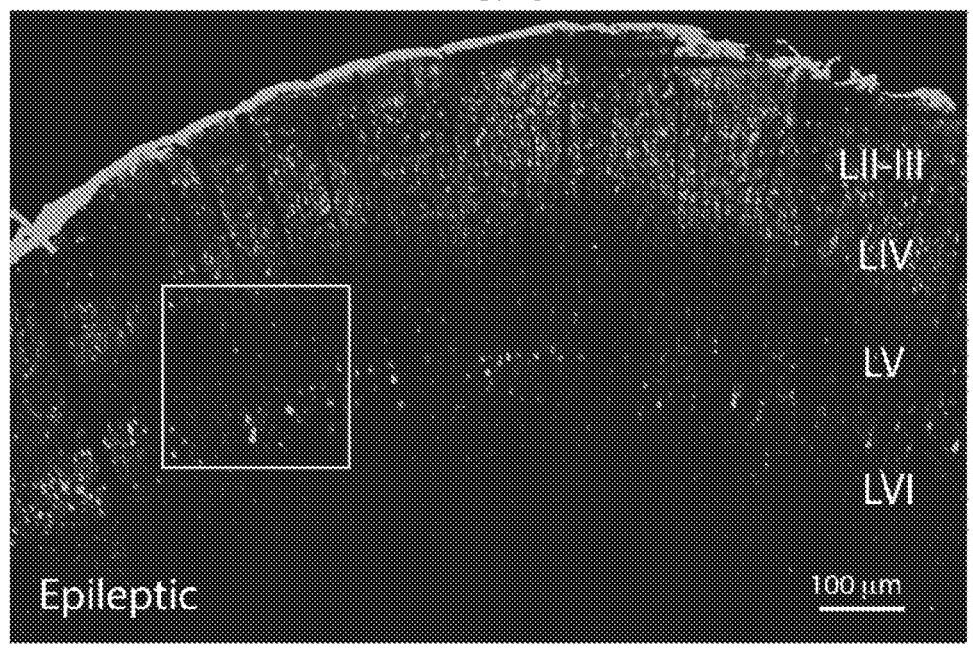
Figure 1D:
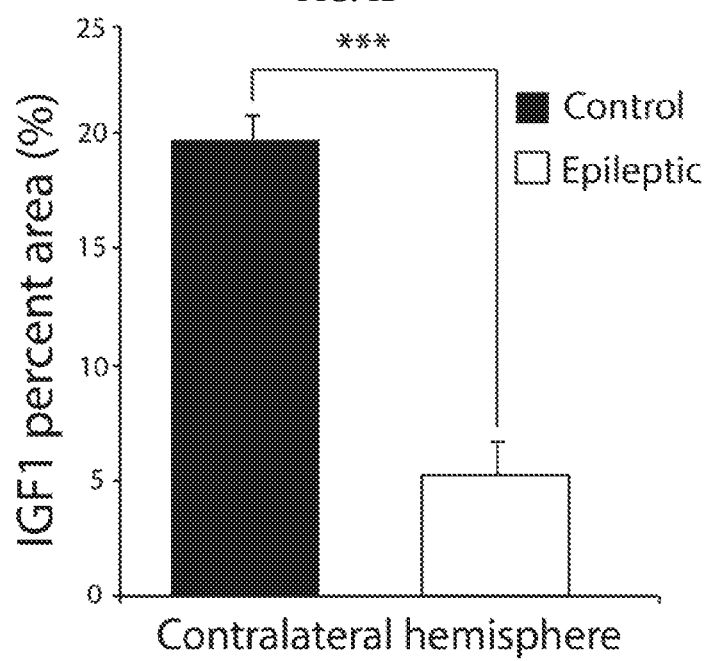
FIG. 1D comprises a graph summarizing the reduced neocortical expression of IGF-1 in a group of epileptic animals compared to normal controls. Areas outlined by the boxes in FIGS. 1A and 1C were subjected to quantitative analysis using IMAMS image analysis software.
Figure 2:
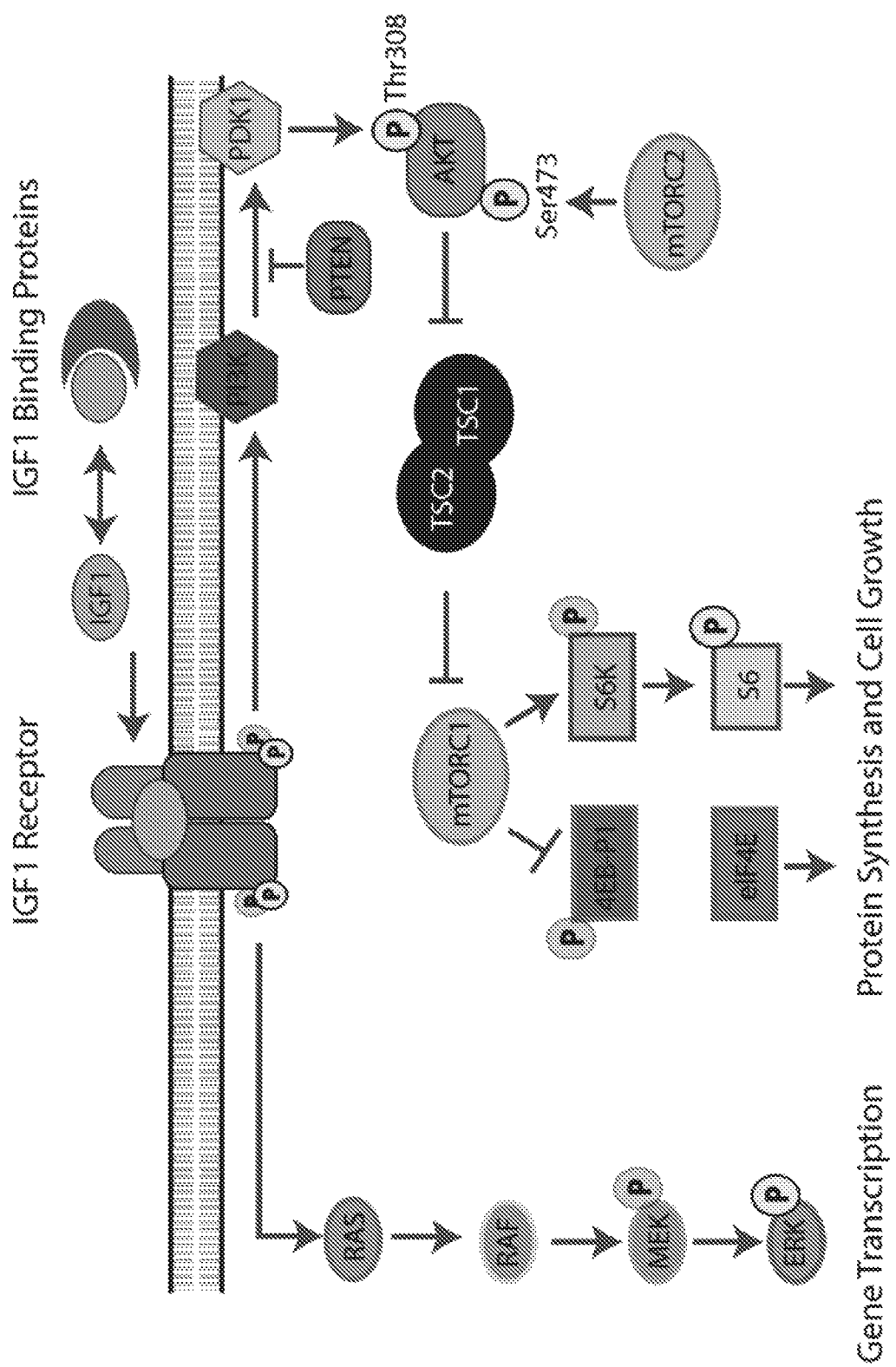
FIG. 2 comprises an illustrative diagram of the IGF-1 signaling pathway. When IGF-1 binds to its receptor, it activates the PI3K-AKT-mTOR signaling cascade. Activation of this pathway can be monitored biochemically and immunohistochemically through changes in the levels of phosphoAKT at Thr308 and Ser473 as well as phosphoS6 at Ser 240/244.
Figure 3A:
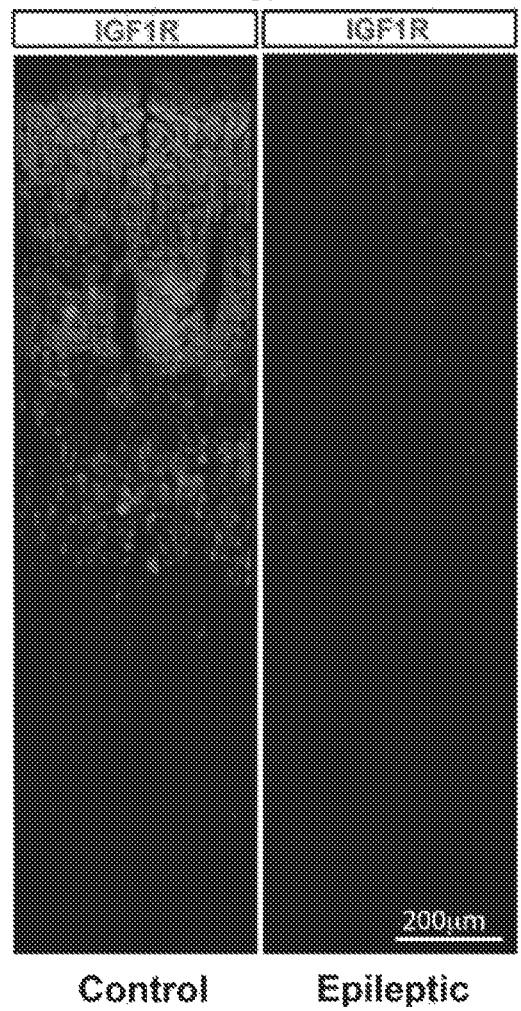
FIGS. 3A-3B comprise images illustrating the finding that IGF-1R is also reduced in epileptic neocortices. Expression levels of the IGF-1 receptor are demonstrated by immunohistochemical methods (FIG. 3A) and by western blotting (FIG. 3B).
Figure 3B:
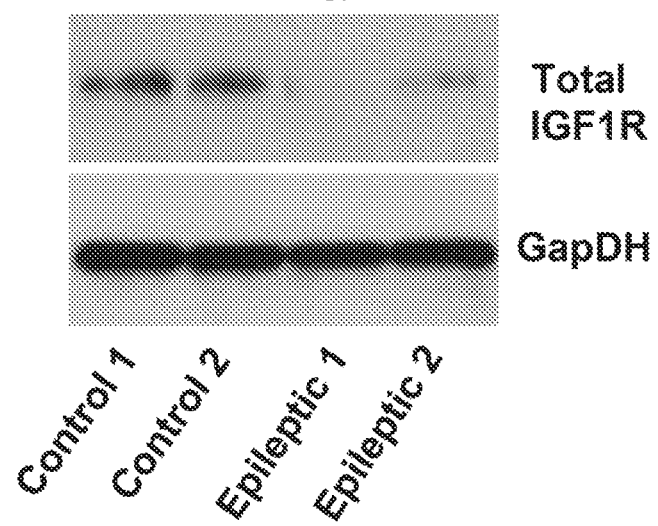
Figure 4A:
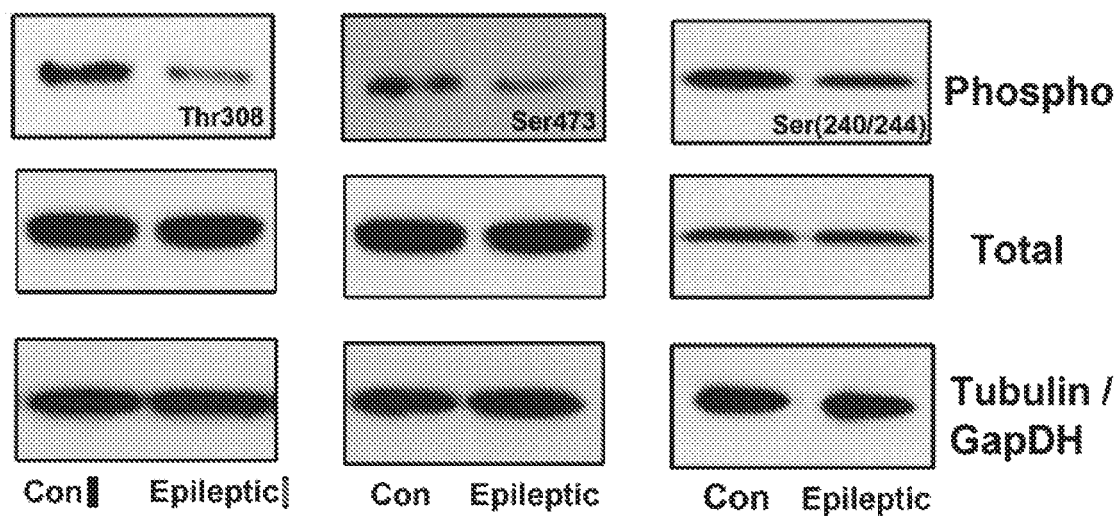
FIG. 4A comprises a series of images of western blots showing suppression of IGF-1 signaling in an epileptic neocortex.
Figure 4B:
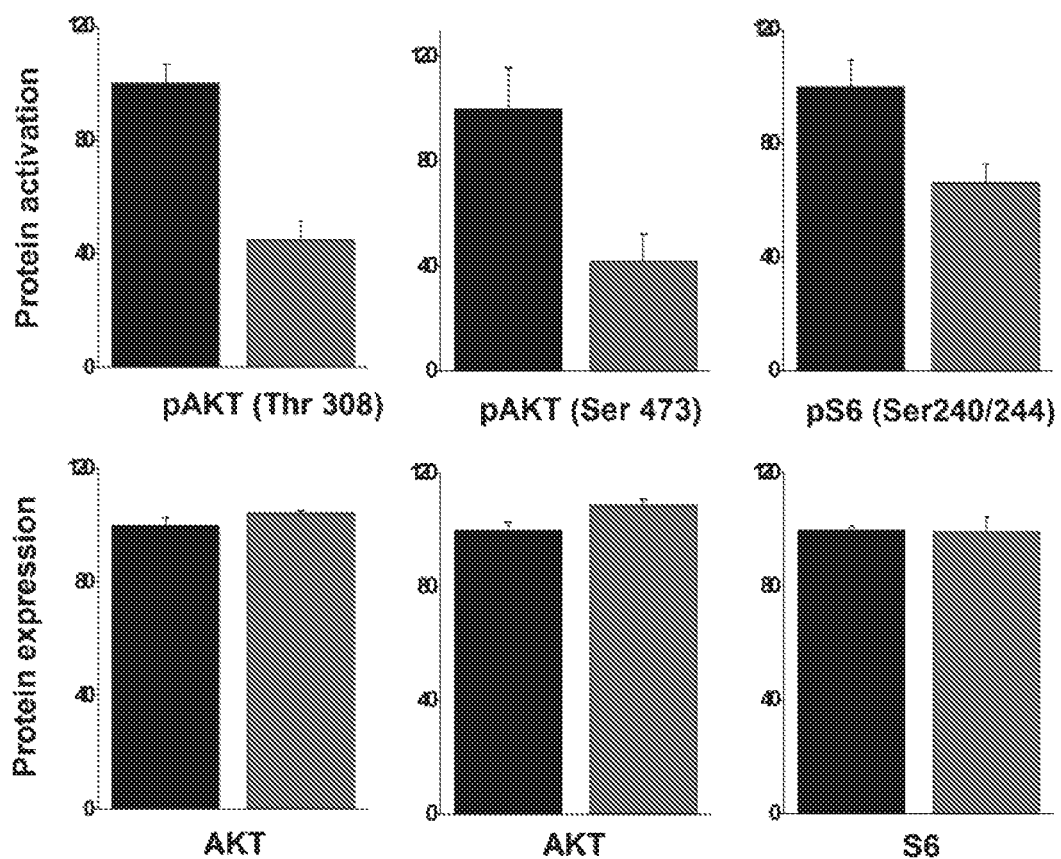
FIG. 4B comprises a series of graphs reporting quantified results from images in FIG. 4A. The western blots demonstrated that levels of phosphoAKT at Thr308 and Ser473 and phosphoS6 at Ser240/244 are all reduced.
Figure 6A:
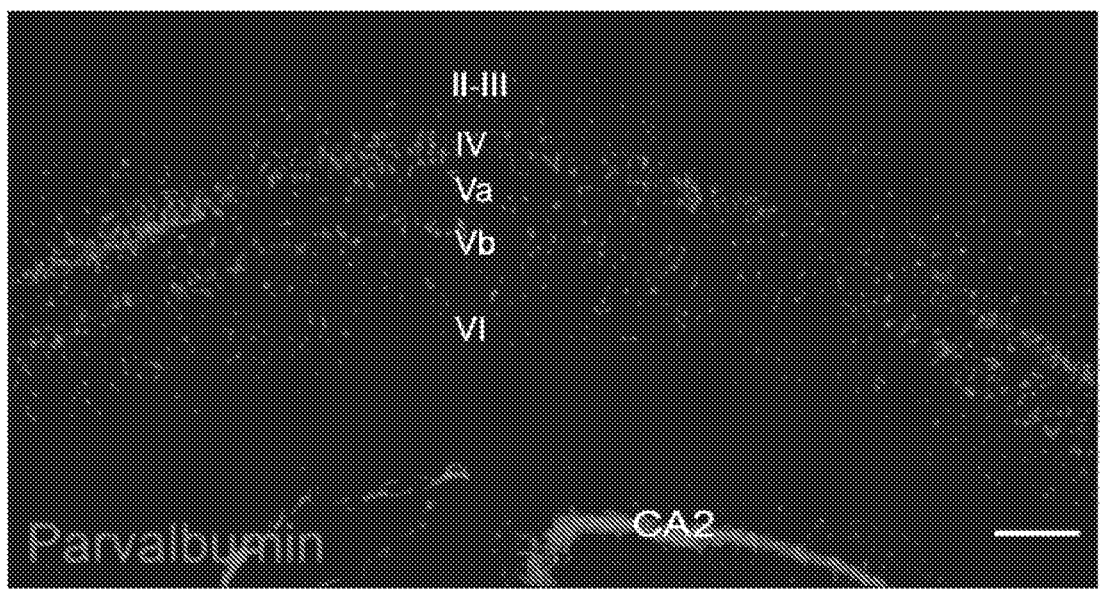
FIGS. 6A-6F comprise a series of images and graphs showing that expression of inhibitory interneuron biomarkers are reduced in the neocortex of animals suffering from spasms.
Figure 6B:
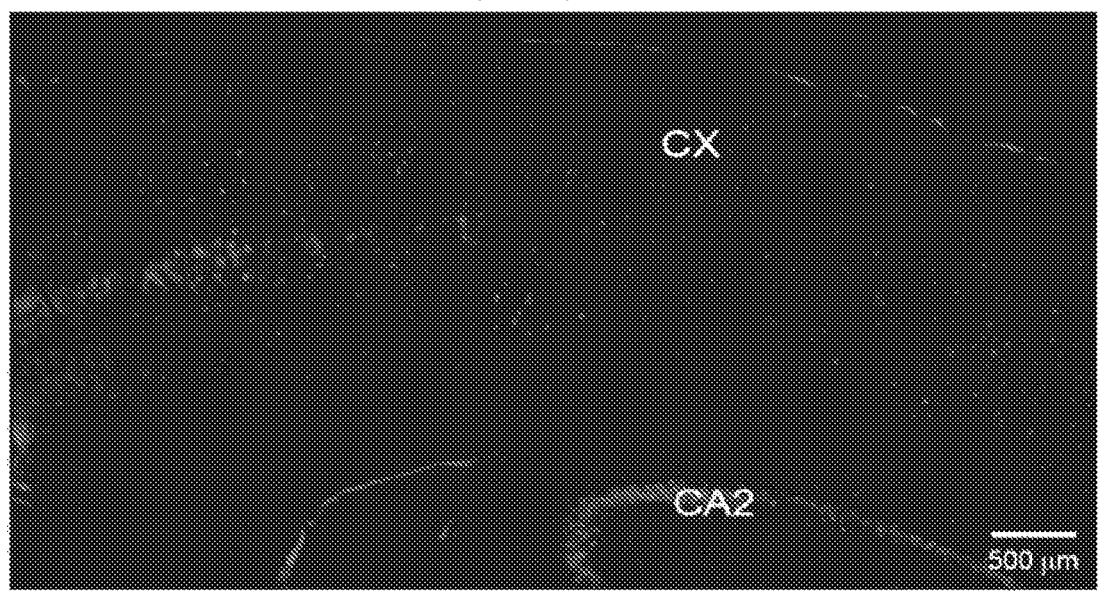
Figure 6C:
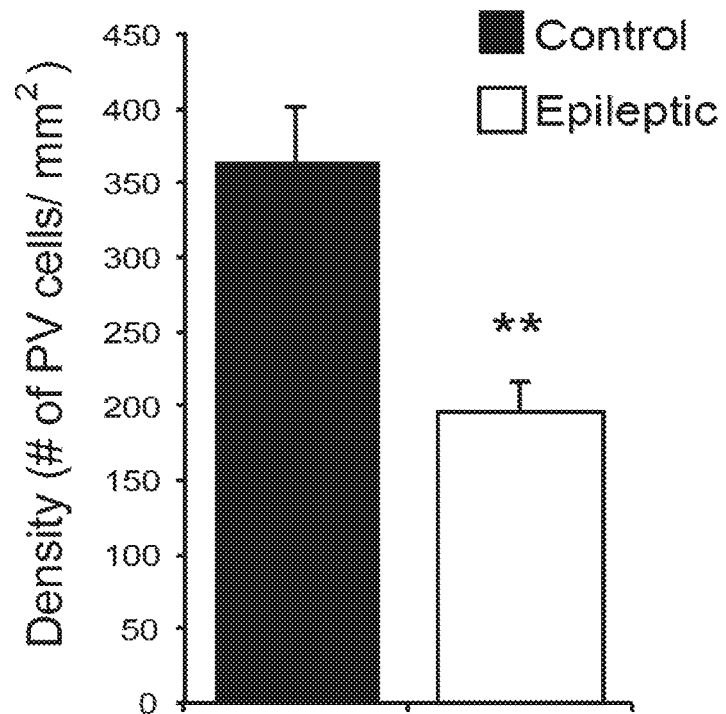
Figure 6D:
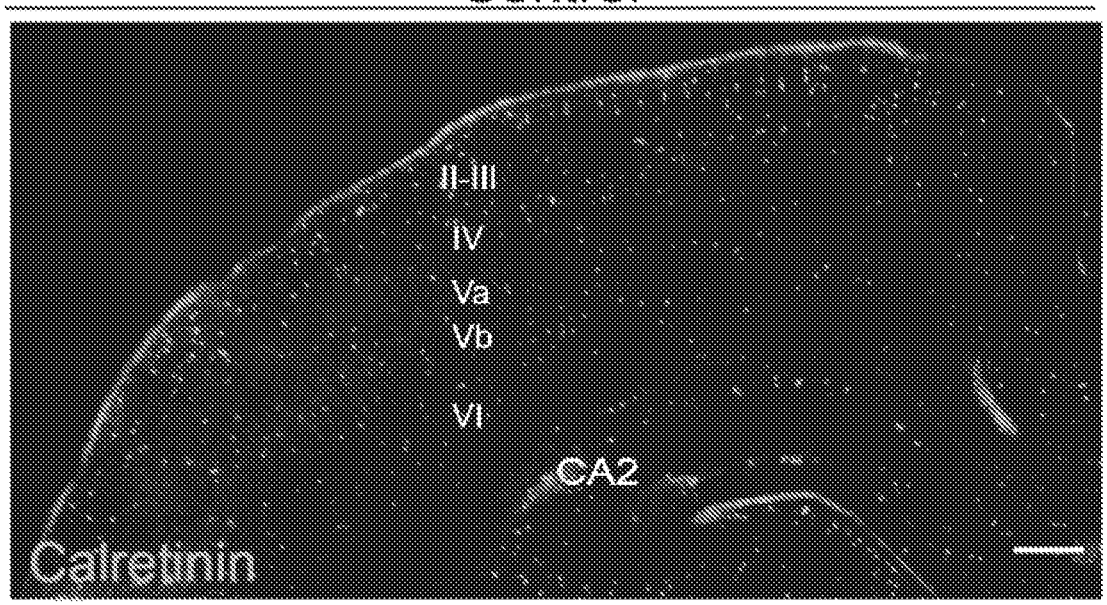
Figure 6E:
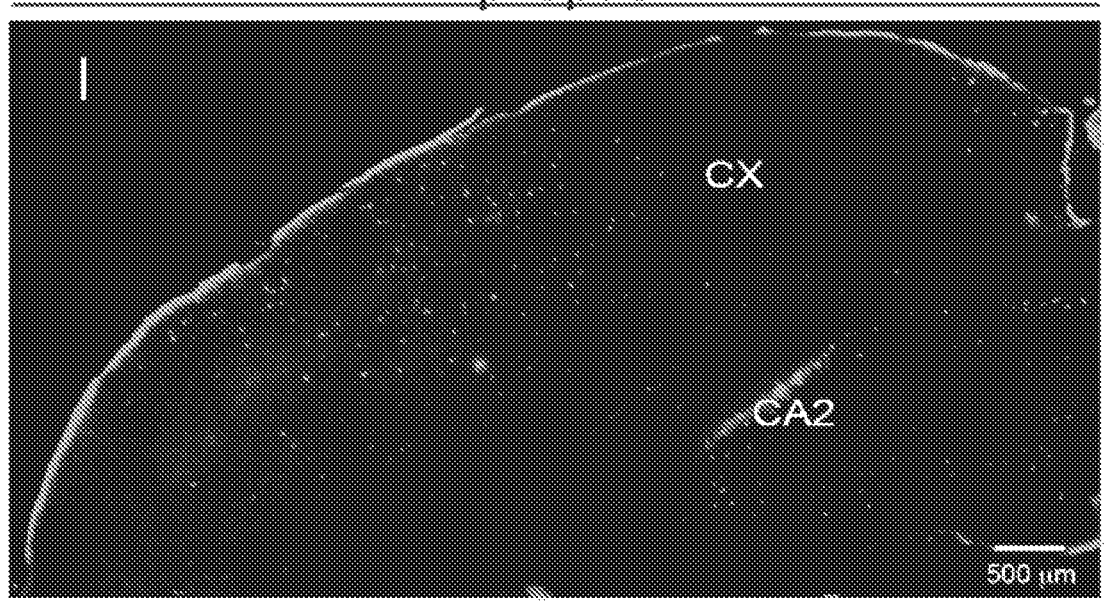
Figure 6F:
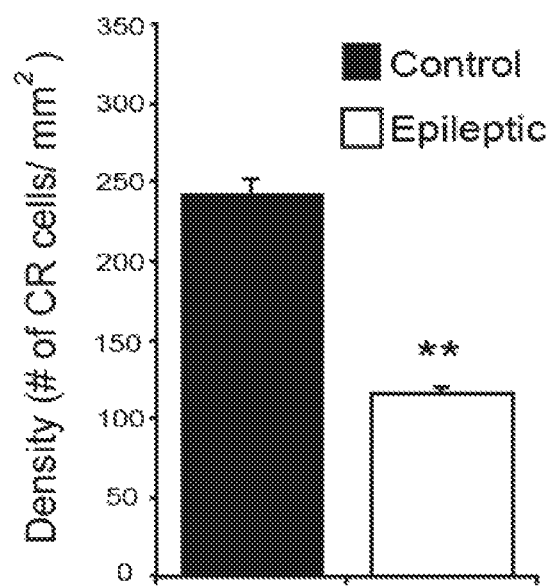
Figure 7C:
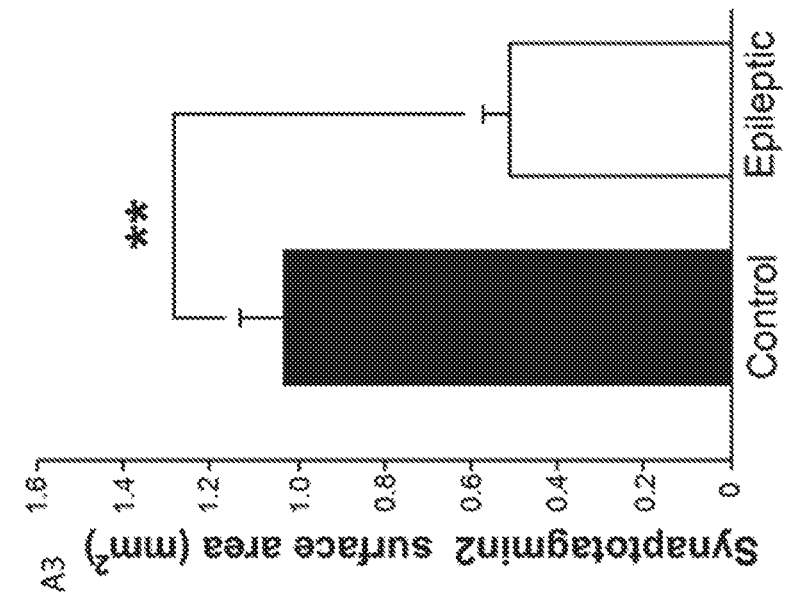
FIGS. 7A-7C comprise images and a graph showing that a specific parvalbumin inhibitory interneuron presynaptic biomarker is reduced in the neocortex of animals suffering from epileptic spasms. Immunohistochemical techniques were used to visualize the expression of synaptotagmin2, a presynaptic molecule that in neocortex is localized only in parvalbumin inhibitory interneuron nerve terminals.
Figures 7A, 7B:
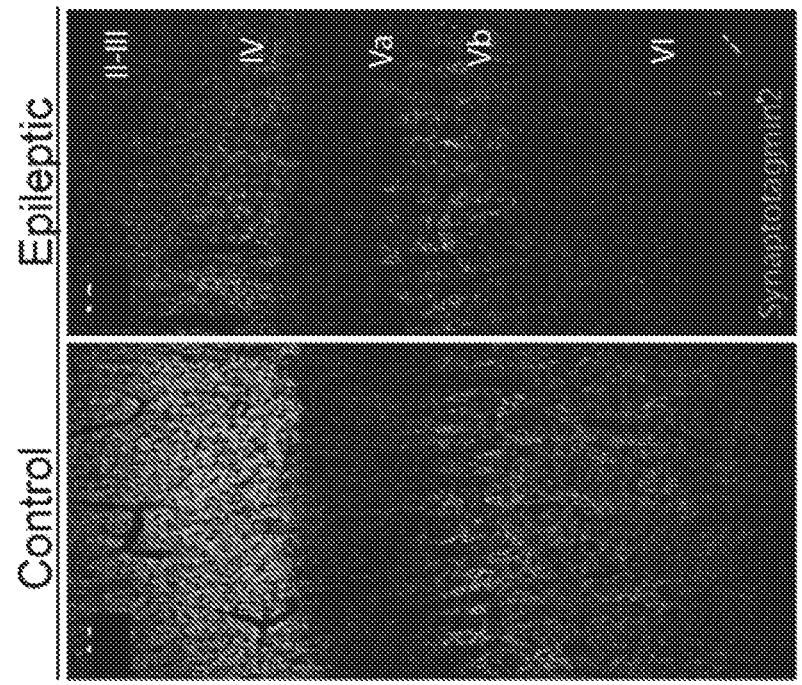

The brains of adult TTX infused rats (40-60 days old) that were verified to have epileptic spasms were perfused for immunohistochemical analysis or frozen for biochemical analysis. Saline-infused rats of the same age served as controls. For immunohistochemistry, sections were stained for IGF-1 or IGF-1R and analyzed by super resolution confocal microscopy. Quantitative analysis of images was undertaken with IMAMS image processing software. Expression levels of both IGF-1 and IGF-1R were found to be depressed in epileptic rats (FIGS. 1A-1D and 3A-3B). Western blotting analysis was undertaken of somatosensory cortex from rats with spasms and their saline-infused control rats. Expression levels of IGF-1R were found to be reduced in epileptic rats (FIG. 3B) as was activation (phosphorylation) of AKT, and S6 (FIGS. 4A-4B). These molecules are actively involved in signaling through the IGf-1R-PI3K-AKT growth pathway (FIG. 2).

Example 2: (1-3)IGF-1 Engagement of IGF-1R-PI3K-Akt Signaling Cascade

Adult Rats (150-175 grams) were injected with 10 mg/kg (1-3)IGF-1 and 1 hour later brains were collected for western blotting. Control rats were injected with vehicle. Western blotting in FIG. 5 revealed a robust activation of the pAKT at Thr308 and Ser473 as well phosphorylation of S6 at Ser240/244. Total AKT and S6 were unaltered. GAPDH served as a loading control.

Example 3: (1-3)IGF-1 Suppression of Spasms

Figure 8A:
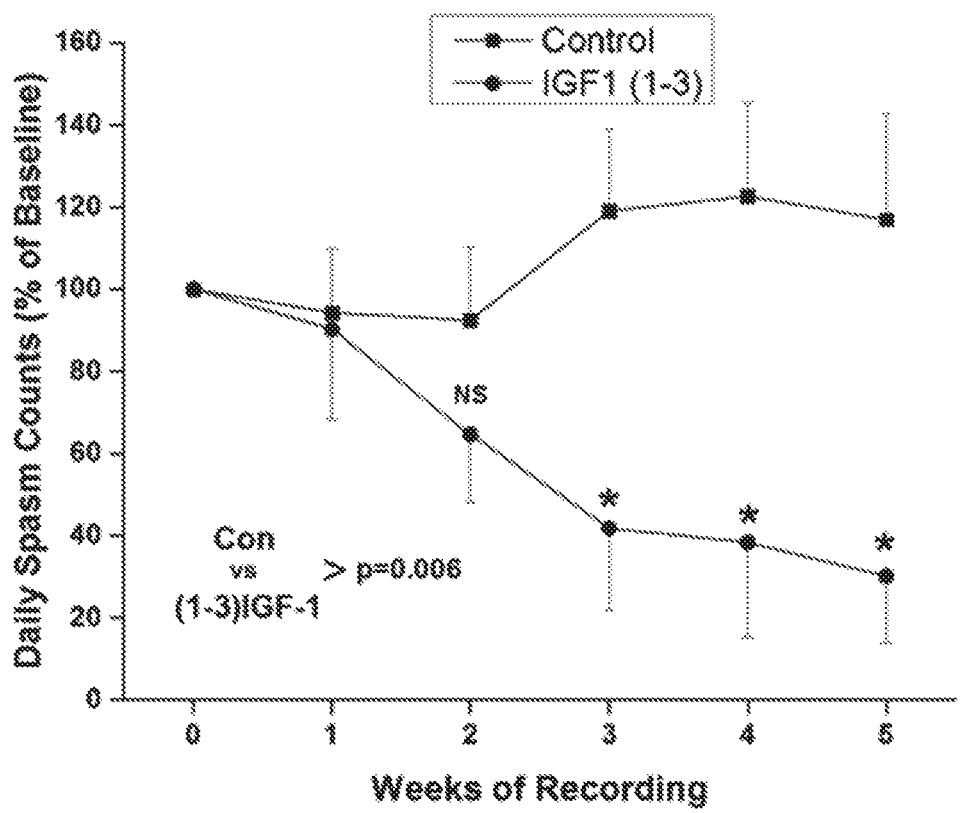
FIGS. 8A-8B comprise a set of graphs showing the suppression of spasms by a 3 week administration of (1-3) IGF-1. The number of epileptic spasms was counted each day for 5 weeks. To do this, video/EEG recordings were conducted 24 hours/day, 7 days/week.
Figure 8B:
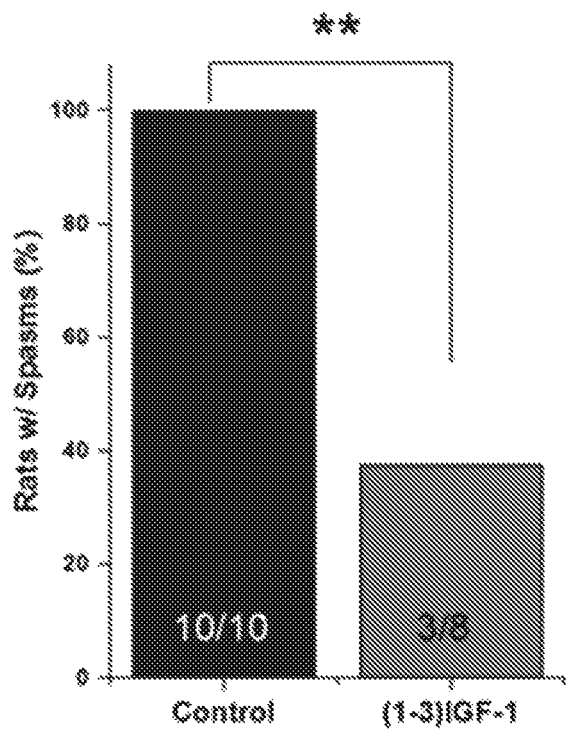
Figure 9D:
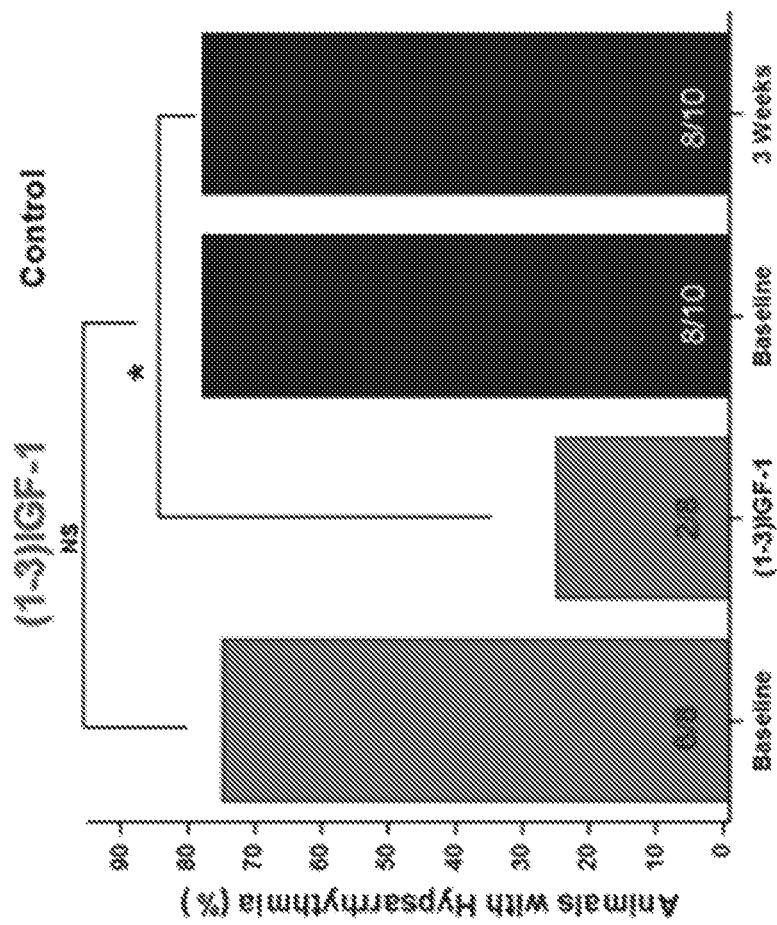
FIG. 9D comprises a graph illustrating effects of (1-3) IGF-1 treatment on hypsarrhythmia in a group of 8 rats in which this abnormal EEG pattern was present in 6 subjects at baseline and was eliminated in 4 of them after treatment. In the control group, all 8 animals that had hypsarrhythmia during baseline continue to have it after treatment with the vehicle for the drug.
Figure 9C:
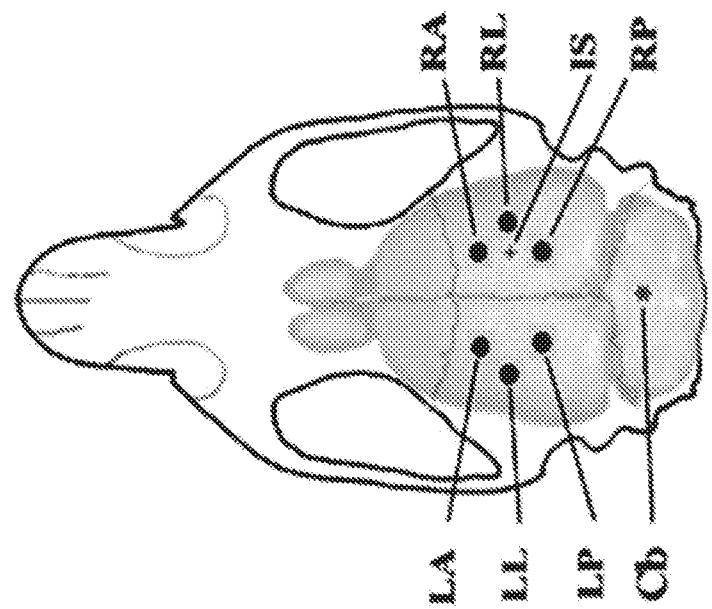
FIG. 9C comprises a diagram showing the electrode placement for the EEG recordings shown in FIGS. 9A-9B.

Rats exhibiting behavioral spasms were implanted with EEG electrodes between postnatal day 27 and 35. Following 5 days of baseline recordings and spasm counting, daily treatment with 10 mg/kg/day of (1-3)IGF-1 was initiated and continued for 3 weeks. Daily spasm counts were obtained for each animal. Counts were averaged at weekly intervals and normalized to baseline spasm counts for each animal. Results in FIG. 8A show that, while control rats continued to have frequent spasms throughout the 5 week recording period, (1-3)IGF-1 treated rats had a gradual and marked reduction in spasm frequency. FIG. 8B shows that 5 of the 8 rats treated with IGF-1 were free of spasms after treatment but all control rats continued to have spasms. Concurrent with counting spasms the EEG recordings were also analyzed for the presence of the highly abnormal EEG pattern, hypsarrhythmia, which is used clinically to diagnose infantile spasms. Recordings in FIG. 9A show hypsarrhythmia in a rat during baseline recordings that was eliminated by (1-3)IGF-1 treatment in FIG. 9B. The bar graphs in FIG. 9D show that the majority of rats that had hypsarrhythmia at baseline no longer had it after treatment. However, control rats that had hypsarrhythmia at baseline continued to have it following treatment with the drug vehicle.

Figure 10B:
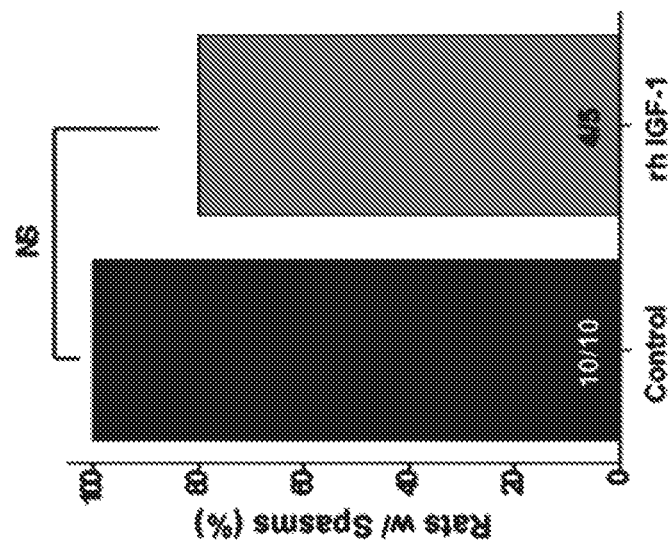
FIGS. 10A-10B comprise hypsarrhythmia graphs showing suppression of spasms by administration of rhIGF-1. Subjects were treated with 1 mg/kg/day of rh(IGF-1) for 3 weeks. Daily spasm counts were averaged over weekly intervals and normalized to baseline counts in each animal. On average, spasm counts were reduced by 40%. One of the 5 treated rats became free of spasms. All control rats continued to have spasms during the 5 weeks of recordings.
Figure 10A:
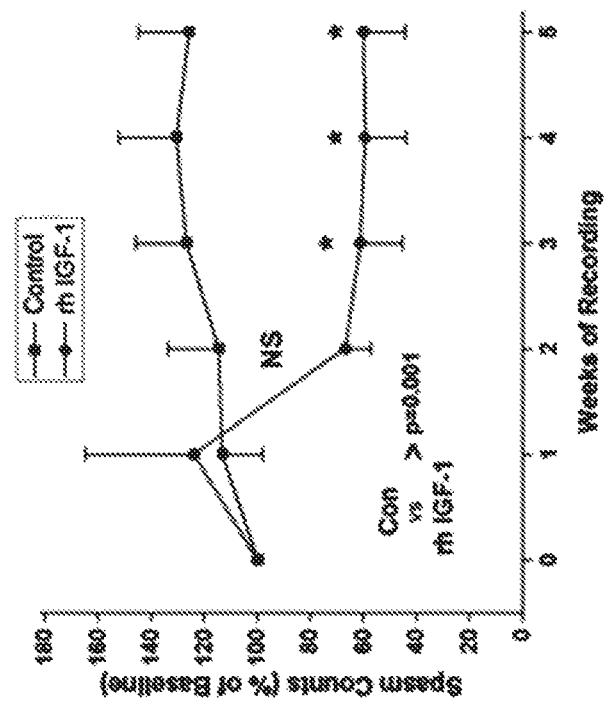
Figure 11I:
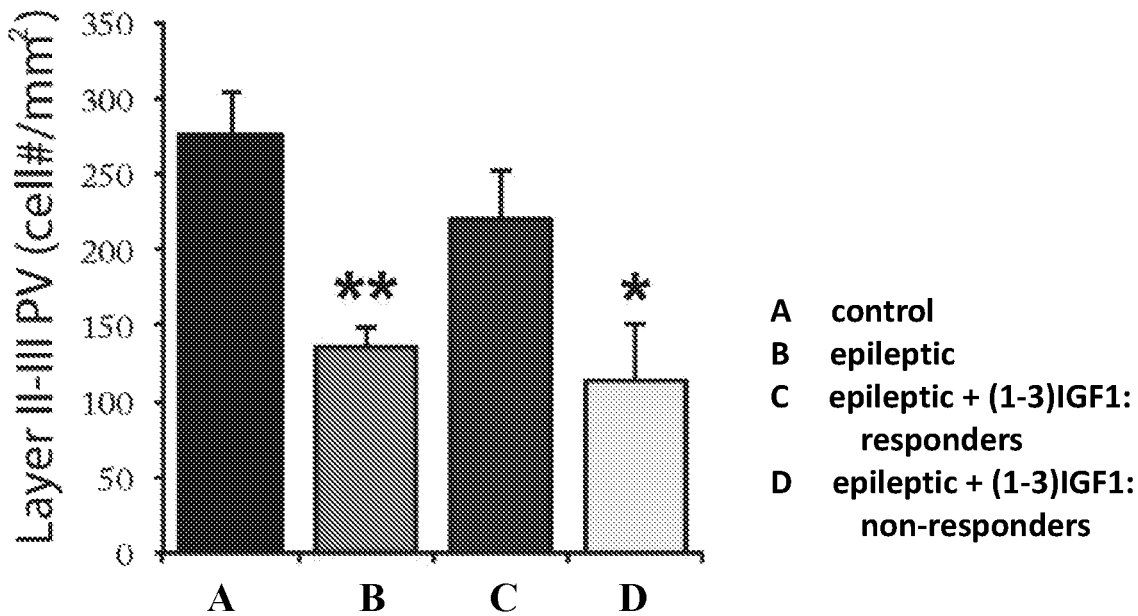
FIG. 11I-11L comprise bar graphs reporting quantified parvalbumin expression (density of cells expressing parvalbumin in 4 neocortical laminae) and show that on average parvalbumin expression is boosted by treatment with (1-3) IGF-1, but only in subjects that became free of spasms.
Figure 11J:
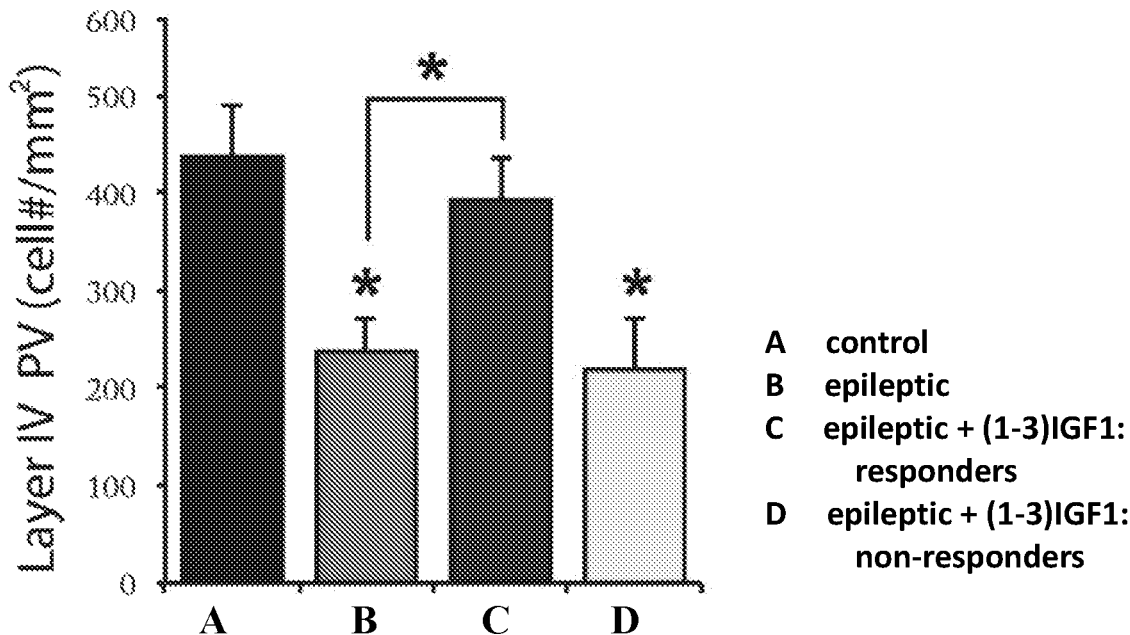
Figure 11K:
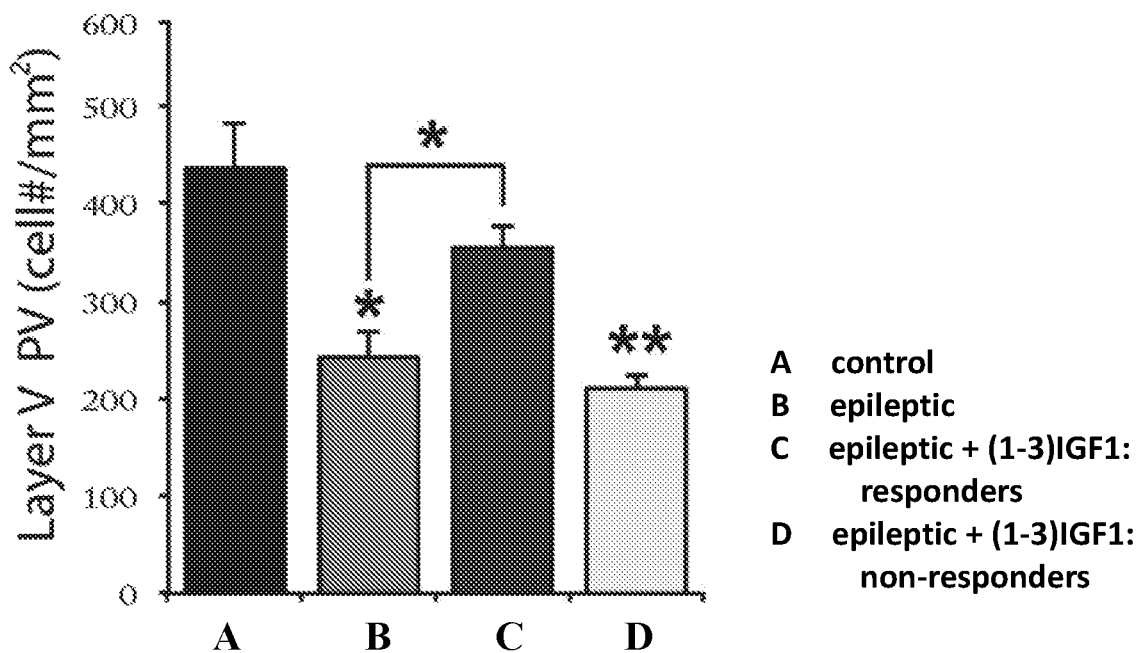
Figure 11L:
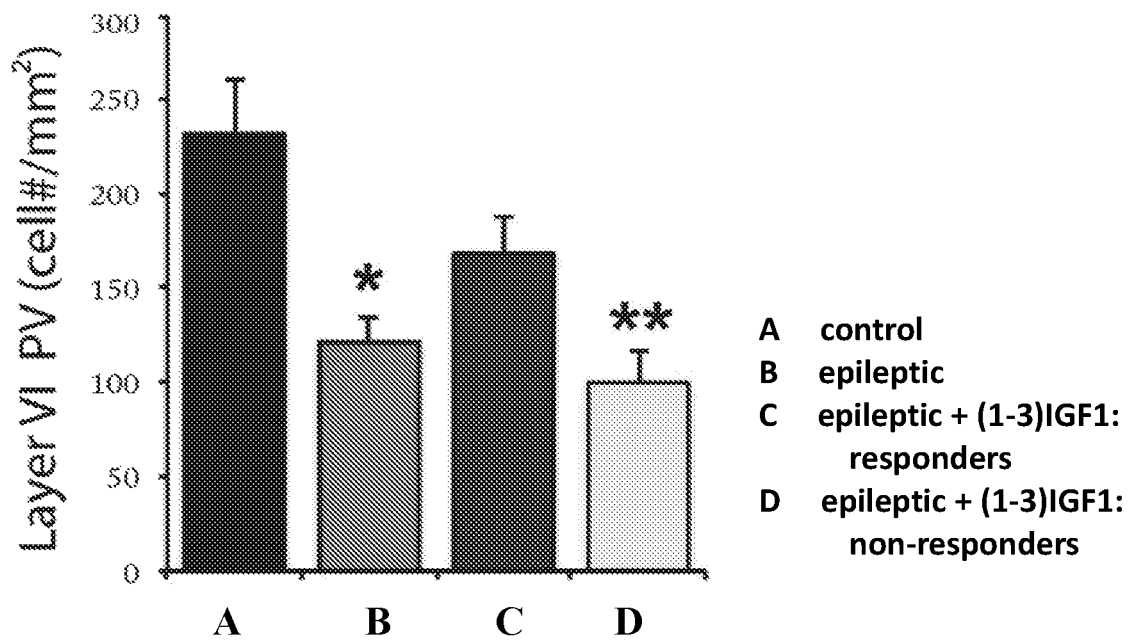

FIGS. 10A-10B show that rhIGF1 at a dose of 1 mg/kg/day also suppressed epileptic spasms. The effects were less than those achieved with (1-3)IGF-1, and the majority (4 of 5) of rats continued to have spasms after 3 weeks of treatment with the full length growth factor.

Following long term video/EEG recordings summarized in FIGS. 8A-8B and 9A-9D, rats were perfused and brain processed for immunohistochemistry. Sections from both control and epileptic rats were stained for parvalbumin, a biomarker for an important subpopulation of inhibitory interneurons. The confocal images and Neurolucida reconstructions in FIGS. 11A-11H show that parvalbumin expression is suppressed in epileptic rats, but expression of this protein is rescued by treatment with (1-3)IGF-1 but only in those animals that responded to the drug and were free of spasms. Non-responding animals still had suppressed levels of parvalbumin. These results are quantified in the bar graphs in FIGS. 11I-11L.

Figure 12:
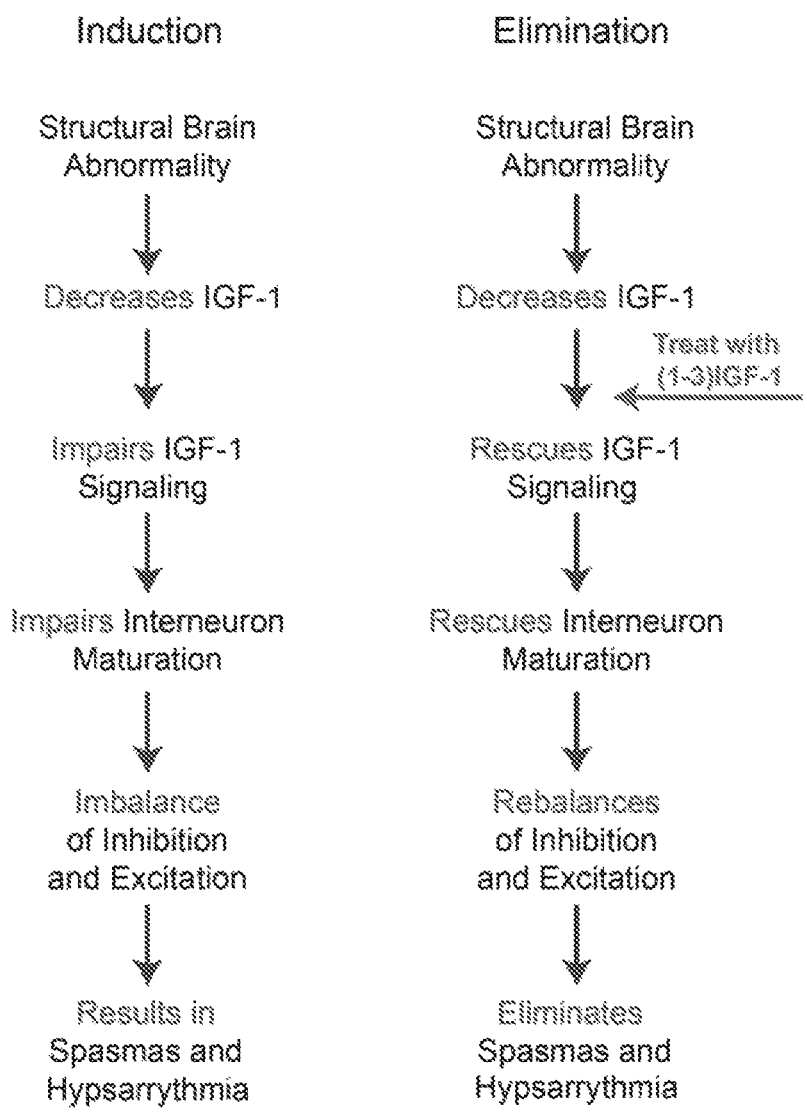
FIG. 12 comprises a flow chart outlining a non-limiting putative mechanism of action for elimination of infantile spasms by (1-3)IGF-1. Without being limited to any one theory, it is hypothesized that an insult to the developing brain results in a loss of IGF-1, and depressed IGF-1 signaling that in turn impairs inhibitory interneuron maturation, which results in an imbalance in inhibition/excitation in the cortex and spasms. It is proposed that treatment with (1-3)IGF-1 serves to replace the missing IGF-1 and rescues IGF-1R signaling and interneuron maturation, and thereby stops epileptic spasms.

FIG. 12 summarizes a working hypothesis on how spasms are induced and how treatment with (1-3)IGF-1 eliminates them. Without being limited to any one particular theory, it is hypothesized that an insult to the developing brain results in a loss of IGF-1 and depressed IGF-1 signaling that in turn impairs inhibitory interneuron maturation which results in an imbalance in inhibition/excitation in the cortex and spasms. It is hypothesized that treatment with (1-3)IGF-1 serves to replace the missing IGF-1 and rescues both IGF-1R signaling and interneuron maturation and thereby stops epileptic spasms.

Example 4: VGB Suppression of Spasms

Video/EEG recordings were used to quantify the number of epileptic spasms rats experienced over a 5 week period. In FIG. 13, a group of rats received 325 mg/kg/day of vigabatrin every day for 2 weeks. Control rats received the drug's vehicle at the same time. Spasm counts were averaged over weekly intervals and normalized to counts during the baseline recordings. Results show a dramatic reduction in spasm counts in the VGB treated animals.

FIG. 14A illustrates recordings of hypsarrhythmia during baseline recordings. After VGB treatment (325 mg/kg/day for 2 weeks) hypsarrhythmia was eliminated. FIG. 14B summarizes the group effects of VGB treatment on hypsarrhythmia. This highly abnormal EEG pattern was eliminated in all VGB-treated rats. However, all control rats that had hypsarrhythmia at baseline continued to have it 2 weeks after initiating treatment with the drug-vehicle.

Example 5: Combination Treatment and Formulations

FIG. 13 shows that vigabatrin at a daily dosage of 325 mg/kg/day is effective in reducing spasm frequency. However, this high dosage has been shown to have toxic side effects. In FIG. 15A, in an attempt to reduce its toxicity, the dosage of VGB was reduced to 250 mg/kg/day for 2 week and co-administered with 10 mg/kg/day of (1-3)IGF-1. Both drugs alone had modest effects on spasm counts; however the combination therapy produced a dramatic reduction in spasms. Fifty percent of the animals receiving the combination treatment became free of spasms, while all of the rats receiving either drug alone for 2 weeks continued to have spasms.

In FIG. 16A, the dosages of VGB was lowered further and at the same time the dosage of (1-3)IGF-1 was increased. A drug ratio of 125 mg/kg/day of VGB and 20 mg/kg/day of (1-3)IGF-1 was the most effective in suppressing spasms. Spasms were nearly completely eliminated in all animals despite having reduced the vigabatrin dosage by 62%. A dosing ratio of 70/40 was unable to abolish spasms.

FIG. 17 compares anticonvulsant effects of a 2 week treatment of 125 mg/kg/day of VGB alone to that of 20 mg/kg/day of (1-3)IGF-1 alone and to the two drugs given in combination. Results show a dramatic synergistic effect of the two drugs.

Example 6: Combination Treatment: Synergy and Efficacy

As demonstrated herein, (1-3)IGF-1 can act synergistically with vigabatrin, when administered in combination to abolish spasms. This synergistic effect is clearly demonstrated by results in the TTX rat model of infantile spasms. Rats were treated for 2 weeks with either (1-3)IGF-1, vigabatrin, or the combination of these two drugs. Drugs were delivered i.p., and N was between 4 and 10 per group.

FIGS. 18A-18C illustrate spasm counts obtained for the various experimental groups. FIG. 18A illustrates effects of high-dose vigabatrin (325 mg/kg/day) on spasm counts. FIG. 18B illustrates effects of individual doses of vigabatrin (250 mg/kg/day), individual doses of (1-3)IGF-1 (10 mg/kg/day), and combination treatment with (1-3)IGF-1 and vigabatrin at the same doses. The combination treatment animals had a lower spasm count that the animals treated with vigabatrin at 325 mg/kg/day. FIG. 18C illustrates effects of individual doses of vigabatrin (125 mg/kg/day), individual doses of (1-3)IGF-1 (20 mg/kg/day), and combination treatment with (1-3)IGF-1 and vigabatrin at the same doses. The combination treatment animals had a lower spasm count that the animals treated with vigabatrin at 325 mg/kg/day or the animals treated with a combination of vigabatrin (250 mg/kg/day) and (1-3)IGF-1 (10 mg/kg/day).

FIGS. 19A-19C illustrate % animals with spasms, as observed for the various experimental groups. FIG. 19A illustrates effects of high-dose vigabatrin (35 mg/kg/day) on % animals with spasms. FIG. 19B illustrates effects of individual doses of vigabatrin (250 mg/kg/day), individual doses of (1-3)IGF-1 (10 mg/kg/day), and combination treatment with (1-3)IGF-1 and vigabatrin at the same doses. Individual administration of 250 mg/kg/day vigabatrin or 10 mg/kg/day (1-3)IGF-1 had no measurable effect of % animals with spasms. In contrast, the combination treatment animals had a similar % animals with spasms as in the case of animals treated with vigabatrin at 325 mg/kg/day. FIG. 19C illustrates effects of individual doses of vigabatrin (125 mg/kg/day), individual doses of (1-3)IGF-1 (20 mg/kg/day), and combination treatment with (1-3)IGF-1 and vigabatrin at the same doses. Individual administration of 125 mg/kg/day vigabatrin or 20 mg/kg/day (1-3)IGF-1 had no measurable effect of % animals with spasms. In contrast, the combination treatment animals had a lower % animals with spasms as in the case of animals treated with vigabatrin at 325 mg/kg/day, and even animals treated with vigabatrin at 250 mg/kg/day and (1-3)IGF-1 at 10 mg/kg/day.

Example 7: Combination Treatment: Reduction of Side Effects

Visual field loss following exposure to vigabatrin is a known clinical development (Maguire et al., 2010, Epilepsia 51:2423-2431). Upon a review of 22 clinical studies (spanning 1,678 vigabatrin-treated subjects versus 406 control subjects), it was determined that 44% of vigabatrin-treated subjects had visual field loss versus 7% of control subjects. Further, 52% of adults and 34% of children had visual field loss in the clinical studies. As a consequence, the current standard of care requires that vigabatrin be reserved for patients with no other alternative treatment, or for those where the benefits outweigh the risk of visual field loss.

To evaluate if the combination treatment showed any advantage in terms of reduced visual field loss over vigabatrin alone, a study comparing retinotoxicity in rats treated with vigabatrin as the single therapeutic agent, or a combination of vigabatrin and (1-3)IGF-1, was performed. Four groups of rats were used (n=7 or 8 per group): Controls, High-dose vigabatrin (325 mg/kg/day), Combination of 125 mg/kg/day vigabatrin and (1-3)IGF-1 20 mg/kg/day, and Low-dose vigabatrin 125/mg/kg/day. All rats were treated for 45 days. After treatment, retina sections were stained, labeling cone photoreceptors with peanut lectin (PNA—red in images), and counter stained with fluorescent Nissl (green). This allowed for staining the cell bodies of neurons and photoreceptors and for evaluating the integrity of retinal cell layers.

FIGS. 20A-20C illustrate the finding that photoreceptors are severely damaged by high-dose vigabatrin but much less so by the combination therapy. FIG. 20A illustrates effects of high-dose vigabatrin and combination therapy integrity of retinal cell layers. FIG. 20B is a bar graph illustrating retinal damage, as determined by quantifying length of the retina with discernable photoreceptor layer damage, and expressing it as percent of total retinal length. FIG. 20C is a bar graph illustrating retinal damage, as determined by counting cone photoreceptors.

Example 8: Combination Treatment: PK Studies

FIG. 21 illustrates plasma concentration for vigabatrin (administered to rats at 125 mg/kg) when administered alone or in combination with (1-3)IGF-1 (20 mg/kg). Co-administration of (1-3)IGF-1 had no discernible effect on vigabatrin pharmacokinetics.

Example 9: IGF-1 Signaling Cascade

Experiments were performed to shed light on certain elements of IGF-1 signaling pathway and how (1-3)IGF-1 affects such pathway.

As illustrated in FIG. 22, (1-3)IGF-1 engages the IGF-1R-PI3K-AKT and IGF-1R-Ras-ERK signaling cascades in neocortex. The experiments were performed using N=5 for both control and epileptic groups. Animals were 6 weeks old and sacrificed 2 hours after treatment.

As illustrated in FIGS. 23A-23D, (1-3)IGF-1 acts through IGF-1R. The neocortex of IGF-1R$^{f/f}$ mice was injected with AAV-Cre virus on P1. Using dTomato as a reporter, tissue punches were taken from transfected region on P25 (FIG. 23A). Western blots show a >75% reduction in IGF-1R (FIGS. 23B-23C). Transfected mice and controls were treated with (1-3)IGF-1 or vehicle on P25. Tissue punches were taken 2 hours later, and it was found that elimination of IGF-1R prevented AKT phosphorylation (FIG. 23D).

As illustrated in FIG. 24, the selective IGF-1R antagonist, picropodophyllin (PPP, or (5R,5aR,8aS,9R)-5-hydroxy-9-(3,4,5-trimethoxyphenyl)-5a,6,8a,9-tetrahydro-5H-[2]benzofuro[5,6-f][1,3]benzodioxol-8-one) blocks (1-3)IGF-1 induced activation of AKT. Animals (6 weeks old) were treated with 50 mg/kg of PPP or DMSO vehicle. Four hours later, they received 20 mg/kg of (1-3)IGF-1 or vehicle. Two hour later the neocortex was collected.

As illustrated in FIGS. 25A-25B, vigabatrin does not activate IGF-1R signaling, and it does not alter (1-3)IGF-1-induced IGF-1R signaling. Vigabatrin (125 mg/kg) was injected 2 and 24 hours before collecting neocortex. Western blots from 2 animals and controls are shown in upper panel (FIG. 25A) for bar graphs n=6. For the combination study, the animals were administered vigabatrin (125/mg/kg), and (1-3)IGF-1 (20 mg/kg) was injected 30 min before collecting cortex in the combination group and the (1-3)IGF-1-only group. Controls received vehicle only. The results are illustrated in FIG. 25B.

Example 10: Oral Administration of IGF-1 Administration

FIG. 26 shows that, when (1-3)IGF-1 is administered orally and in combination with vigabatrin (i.p.), the effects on spasms counts are much greater than when giving vigabatrin alone.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating or ameliorating recurring seizures in a subject, wherein the seizures are derived from at least one disorder selected from the group consisting of infantile spasms, refractory complex partial epilepsy, secondary generalized seizures, simple partial seizures, and refractory seizures, the method comprising administering to the subject a therapeutically effective amount of vigabatrin and a therapeutically effective amount of an IGF-1 agent, wherein the IGF-1 agent comprises at least one of (i)-(iv) or a salt, solvate, enantiomer, or diastereomer thereof:

(i) IGF-1, optionally wherein at least one amide group thereof is methylated, at least one acid residue thereof is derivatized as an amide, at least one acid residue thereof is derivatized as a $C_1$-$C_6$ ester, or a combination thereof;

(ii) (1-3)IGF-1;

(iii) des(1-3)IGF-1, optionally wherein at least one amide group thereof is methylated, at least one acid residue thereof is derivatized as an amide, at least one acid residue thereof is derivatized as a $C_1$-$C_6$ ester, or a combination thereof; and (iv) cyclic prolylglycine, optionally wherein an amide group thereof is methylated.

2. The method of claim 1, wherein the IGF-1 agent is (i), or a salt or solvate thereof.

3. The method of claim 1, wherein the IGF-1 agent is (ii), (iii), or (iv), or an enantiomer, diastereoisomer, salt, or solvate thereof.

4. The method of claim 1, wherein the vigabatrin and the IGF-1 agent are administered simultaneously to the subject.

5. The method of claim 4, wherein the vigabatrin and the IGF-1 agent are co-formulated in a pharmaceutical composition.

6. The method of claim 1, wherein at least one applies: (a) the IGF-1 agent is administered orally to the subject; (b) vigabatrin is administered orally to the subject; (c) the vigabatrin and the IGF-1 agent are co-formulated for oral administration to the subject.

7. The method of claim 1, wherein the vigabatrin is administered to the subject before the IGF-1 agent or wherein the vigabatrin is administered to the subject after the IGF-1 agent.

8. The method of claim 1, wherein the vigabatrin is administered to the subject in a dose of (a) about 50 mg/kg/day to about 400 mg/kg/day, (b) about 100 mg/kg/day to about 250 mg/kg/day, or (c) about 125 mg/kg/day.

9. The method of claim 1, wherein the IGF-1 agent is administered to the subject in a dose of about 1 mg/kg/day to about 200 mg/kg/day.

10. The method of claim 9, wherein the IGF-1 agent is administered to the subject in a dose of about 20 mg/kg/day.

11. The method of claim 1, wherein the therapeutically effective amount of vigabatrin when administered in conjunction with the IGF-1 agent is lower than a therapeutically effective amount of vigabatrin to be administered in the absence of the IGF-1 agent.

12. The method of claim 1, wherein the therapeutically effective amount of the IGF-1 agent when administered in conjunction with vigabatrin is lower than a therapeutically effective amount of the IGF-1 agent to be administered in the absence of vigabatrin.

13. The method of claim 1, wherein the subject suffers a reduced or negligible vigabatrin-related side effect, as compared to treatment with vigabatrin in the absence of the IGF-1 agent.

14. The method of claim 13, wherein the vigabatrin-related side effect is at least one selected from the group consisting of retinotoxicity, visual field loss, neurotoxicity, peripheral neuropathy, renal complications, drowsiness, headache, dizziness, anxiety, depression, memory loss, impairment of cognitive development, diplopia, aggression, ataxia, vertigo, hyperactivity, vision loss, retinal nerve fiber damage, confusion, insomnia, impaired concentration, speech disorders, irritability, tremors, emotional lability, and abnormal gait.

15. The method of claim 13, wherein the vigabatrin-related side effect is at least one from the group consisting of retinotoxicity and visual field loss.

16. The method of claim 1, wherein the subject experiences (a) more than 90% spasm reduction upon the administering, (b) more than 95% spasm reduction upon the administering, or (c) about 100% spasm reduction upon the administering.

17. The method of claim 1, wherein the subject is a mammal.

18. The method of claim 17, wherein the subject is a human.

19. The method of claim 1, wherein the IGF-1 agent comprises at least one of (i), (iii), and (iv) or a salt, solvate, enantiomer, or diastereomer thereof:

(i) IGF-1, wherein at least one amide group thereof is methylated, at least one acid residue thereof is derivatized as an amide, at least one acid residue thereof is derivatized as a $C_1$-$C_6$ ester, or a combination thereof;

(iii) des(1-3)IGF-1, wherein at least one amide group thereof is methylated, at least one acid residue thereof is derivatized as an amide, at least one acid residue thereof is derivatized as a $C_1$-$C_6$ ester, or a combination thereof; and (iv) cyclic prolylglycine, wherein an amide group thereof is methylated.

20. A method of treating or ameliorating recurring seizures in a subject, wherein the seizures are derived from at least one disorder selected from the group consisting of infantile spasms, refractory complex partial epilepsy, secondary generalized seizures, simple partial seizures, and refractory seizures, the method comprising administering to the subject a therapeutically effective amount of an IGF-1 agent, wherein the subject is not administered any other agent that treats or ameliorates seizures, and wherein the IGF-1 agent comprises at least one of (i)-(iv) or a salt, solvate, enantiomer, or diastereomer thereof:

(i) IGF-1, optionally wherein at least one amide group thereof is methylated, at least one acid residue thereof is derivatized as an amide, at least one acid residue thereof is derivatized as a $C_1$-$C_6$ ester, or a combination thereof;

(ii) (1-3)IGF-1;

(iii) des(1-3)IGF-1, optionally wherein at least one amide group thereof is methylated, at least one acid residue thereof is derivatized as an amide, at least one acid residue thereof is derivatized as a $C_1$-$C_6$ ester, or a combination thereof; and (iv) cyclic prolylglycine, optionally wherein an amide group thereof is methylated, or a combination thereof.

21. The method of claim 20, wherein the IGF-1 agent comprises at least one of (i), (iii), and (iv) or a salt, solvate, enantiomer, or diastereomer thereof:

(i) IGF-1, wherein at least one amide group thereof is methylated, at least one acid residue thereof is derivatized as an amide, at least one acid residue thereof is derivatized as a $C_1$-$C_6$ ester, or a combination thereof;

(iii) des(1-3)IGF-1, wherein at least one amide group thereof is methylated, at least one acid residue thereof is derivatized as an amide, at least one acid residue thereof is derivatized as a $C_1$-$C_6$ ester, or a combination thereof; and (iv) cyclic prolylglycine, wherein an amide group thereof is methylated.

* * * * *

SEQUENCE LISTING

<160> NUMBER OF SEQ ID NOS: 1

<210> SEQ ID NO 1
<211> LENGTH: 70
<212> TYPE: PRT

```
<213> ORGANISM: Artificial Sequence
<220> FEATURE:
<223> OTHER INFORMATION: Chemically Synthesized

<400> SEQUENCE: 1

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65              70
```